(12) United States Patent
Chambon et al.

(10) Patent No.: US 6,653,322 B1
(45) Date of Patent: Nov. 25, 2003

(54) THERAPEUTIC COMBINATIONS OF RAR ANTAGONISTS AND RXR AGONISTS AND USE THEREOF

(75) Inventors: Pierre Chambon, Blaesheim (FR); Hinrich Gronemeyer, Oberkirch (DE); Peter R. Reczek, East Amherst, NY (US); Jacek Ostrowski, Getzville, NY (US)

(73) Assignees: Bristol-Myers Squibb Company, Princeton, NJ (US); Institut National de la Sante et de la Recherche Medicale, Paris (FR); Centre National de la Recherche Scientifique, Paris (FR); Universite Louis Pasteur, Strasbourg (FR)

(*) Notice: Subject to any disclaimer, the term of this patent is extended or adjusted under 35 U.S.C. 154(b) by 32 days.

(21) Appl. No.: 09/619,308

(22) Filed: Jul. 19, 2000

Related U.S. Application Data

(62) Division of application No. 09/919,318, filed on Aug. 28, 1997.
(60) Provisional application No. 60/024,772, filed on Aug. 28, 1996.

(51) Int. Cl.$^7$ ............................................. A61K 31/47
(52) U.S. Cl. ........................ 514/311; 514/558; 514/559; 514/560; 514/561; 514/562; 514/563; 514/564; 514/565; 514/566; 514/567; 514/568; 514/569; 514/570; 514/571; 514/572; 514/463; 514/467; 514/725
(58) Field of Search ................................ 514/558–572, 514/463–467, 725

(56) References Cited

U.S. PATENT DOCUMENTS

| | | | |
|---|---|---|---|
| 5,399,586 A | 3/1995 | Davies et al. | 514/448 |
| 5,559,248 A | 9/1996 | Starrett, Jr. et al. | 549/79 |
| 5,702,914 A | 12/1997 | Evans et al. | 435/29 |
| 5,747,661 A | 5/1998 | Evans et al. | 536/24.1 |
| 5,780,676 A | 7/1998 | Boehm et al. | 562/490 |

FOREIGN PATENT DOCUMENTS

| | | |
|---|---|---|
| CA | 2100582 | 9/1992 |
| CA | 2210248 | 7/1996 |
| CA | 2230637 | 3/1997 |
| WO | WO 94/26100 | 11/1994 |
| WO | WO 96/33716 | 10/1996 |
| WO | WO 98/29113 | 7/1998 |
| WO | WO 98/29120 | 7/1998 |
| WO | WO 98/48825 | 11/1998 |

OTHER PUBLICATIONS

Chambon, P., "A Decade of molecular biology of retinoic acid receptors," *FASEB J.* 10:940–954, Jul. 1996.*
Alcalay, M., et al., "Translocation breakpoint of acute promyelocytic leukemia lies within the retinoic acid receptor α locus," *Proc. Natl. Acad. Sci. USA* 88(5):1977–1981 (1991).
Allenby, G., et al., "Binding of 9–cis–Retinoic Acid and All–trans–Retinoic Acid to Retinoic Acid Receptors α, β, and γ," *J. Biol. Chem.* 269(24):16689–16695 (1994).
Allenby, G., "The Ying–yang of RAR and AP–1: cancer treatment without overt toxicity," *Human and Exper. Toxicol.* 14:226–230 (1995).
Anglard, P., et al., "Structure and Promoter Characterization of the Human Stromelysin–3 Gene," *J. Biol. Chem.* 270:20337–20344 (1995).
Apfel, C., et al., "A retinoic acid receptor α antagonist selectively counteracts retinoic acid effects," *Proc. Natl. Acad. Sci. USA* 89(15):7129–7133 (1992).
Apfel, C.M., et al., "Enhancement of HL–60 Differentiation by a New Class of Retinoids with Selective Activity on Retinoid X Receptor," *J. Biol. Chem.* 270(51):30765–30772 (Dec. 22, 1995).
Åström, A., et al., "Retinoic Acid and Synthetic Analogs Differentially Activate Retinoic Acid Receptor Dependent Transcription," *Biochem. Biophys. Res. Comm.* 173(1):339–349 (1990).
Bérard, J., et al., "Lung tumors in mice expressing an antisense RARβ2 transgene," *FASEB J.* 10:1091–1097 (Jul. 1996).
Bernard, B.A., et al., "Identification of Synthetic Retinoids with Selectivity for Human Nuclear Retinoic Acid Receptor γ," *Biochem. Biophys. Res. Comm.* 186(2):977–983 (1992).
Bollag, W., and Holdener, E.E., "Retinoids in cancer prevention and therapy," *Annals of Oncol.* 3(7):513–526 (1992).
Bollag, W., et al., "Cancer Combination Chemotherapy with Retinoids: Experimental Rationale," *Leukemia* 8(9):1453–1457 (1994).
Bollag, W., "The retinoid revolution," *FASEB J.* 10:938–939 (Jul. 1996).
Bonhomme, L., et al., "Topical treatment of epidemic Kaspoi's sarcoma with all–trans–retinoic acid," *Annals of Oncol.* 2(3):234–235 (1991).
Bourguet, W., et al., "Crystal structure of the ligand–binding domain of the human nuclear receptor RXR–α," *Nature* 375:377–382 (Jun. 1, 1995).
Brand, N., et al., "Identification of a second human retinoic acid receptor," *Nature* 332:850–853 (1988).

(List continued on next page.)

*Primary Examiner*—Dwayne C. Jones
(74) *Attorney, Agent, or Firm*—Sterne, Kessler, Goldstein & Fox, P.L.L.C.

(57) ABSTRACT

The present invention provides compositions and methods for treating an animal, preferably a human, suffering from or predisposed to a physical disorder by administering an effective amount of a composition comprising at least one RAR antagonist, preferably an RARα antagonist, and at least one RXR agonist. The combination of an RXR agonist, which has no therapeutic effects alone, with an RAR antagonist allows the use of lower doses of the RAR antagonist than were previously thought to be efficacious; this approach obviates many of the undesirable physiological side-effects of treatment with RAR antagonists.

24 Claims, 9 Drawing Sheets

OTHER PUBLICATIONS

Brooks III, S.C., et al., "Myeloid Differentiation and Retinoblastoma Phosphorylation Changes in HL–60 Cells Induced by Retinoic Acid Receptor– and Retinoid X Receptor–Selective Retinoic Acid Analogs," *Blood* 87(1):227–237 (Jan. 1, 1996).

Castaigne, S., et al., "All–Trans Retinoic Acid as a Differentiation Therapy for Acute Promyelocytic Leukemia. I. Clinical Results," *Blood* 76(9):1704–1709 (1990).

Chambon, P., "The retinoid signaling pathway: molecular and genetic analyses," *Cell Biol.* 5(2):115–125 (1994).

Chambon, P., "A decade of molecular biology of retinoic acid receptors," *FASEB J.* 10:940–954 (Jul. 1996).

Chandraratna, R.A.S., et al., "Development of RAR subtype Selective Retinoids for Dermatological Diseases," *Eur. J. Med. Chem.* 30:505S–517S (1995).

Chang, K.–S., et al., "Rearrangement of the Retinoic Acid Receptor Gene in Acute Promyelocytic Leukemia," *Leukemia* 5(3):200–204 (1991).

Chen, J.–Y., et al., "RAR–specific agonist/antagonists which dissociate transactivation and AP1 transrepression inhibit anchorage–independent cell proliferation," *EMBO J.* 14(6):1187–1197 (Mar. 1995).

Chen, J.–Y., et al., "Two distinct actions of retinoid–receptor ligands," *Nature* 382:819–822 (Aug. 29, 1996).

Chen, S.–J., et al., "Rearrangements in the Second Intron of the RARA Gene Are Present in a Large Majority of Patients With Acute Promyelocytic Leukemia and Are Used as Molecular Marker for Retinoic Acid–Induced Leukemic Cell Differentiation," *Blood* 78(10):2696–2701 (1991).

Chen, Z., et al., "The Retinoic Acid Alpha Receptor Gene is Frequently Disrupted in its 5' Part in Chinese Patients with Acute Promyelocytic Leukemia," *Leukemia* 5(4):288–292 (1991).

Chiesa, F., et al., "Prevention of Local Relapses and New Localisations of Oral Leukoplakias with the Synthetic Retinoid Fenretinide (4–HPR). Preliminary Results," *Oral Oncol., Eur. J. Cancer* 28B(2):97–102 (1992).

Chomienne, C., et al., "All–Trans Retinoic Acid in Acute Promyelocytic Leukemias. II. In Vitro Studies: Structure-Function Relationship," *Blood* 76(9):1710–1717 (1990).

Chomienne, C., et al., "All–trans Retinoic Acid Modulates the Retinoic Acid Receptor–α in Promyelocytic Cells," *J. Clin. Invest.* 88:2150–2154 (1991).

Chomienne, C., et al., "Retinoid differentiation therapy in promyelocytic leukemia," *FASEB J.* 10:1025–1030 (Jul. 1996).

Costa, A., et al., "Prospects of Chemoprevention of Human Cancers with the Synthetic Retinoid Fenretinide," *Cancer Res.* 54(Suppl.):2032s–2037s (1994).

de Thé, H., et al., "The PML–RARα Fusion mRNA Generated by the t(15;17) Translocation in Acute Promyelocytic Leukemia Encodes a Functionally Altered RAR," *Cell* 66:675–684 (1991).

de Thé, H., "Altered retinoic acid receptors," *FASEB J.* 10:955–960 (Jul. 1996).

Dey, A., et al., "Ligand–Dependent Occupancy of the Retinoic Acid Receptor β2 Promoter In Vivo," *Mol. Cell. Biol.* 14(12):8191–8201 (1994).

Doucas, V., et al., "The PML–retinoic acid receptor α translocation converts the receptor from an inhibitor to a retinoic acid–dependent activator of transcription factor AP–1," *Proc. Natl. Acad. Sci. USA* 90:9345–9349 (1993).

Durand, B., et al., "All–Trans and 9–Cis Retinoic Acid Induction of CRABPII Transcription Is Mediated by RAR-RXR Heterodimers Bound to DR1 and DR2 Repeated Motifs," *Cell* 71:73–85 (1992).

Durand, B., et al., "Activation function 2 (AF–2) of retinoic acid receptor and 9–cis retinoic acid receptor: presence of a conserved autonomous constitutive activating domain and influence of the nature of the response element on AF–2 activity," *EMBO J.* 13(22):5370–5382 (1994).

Dyck, J.A., et al., "A Novel Macromolecular Structure Is a Target of the Promyelocyte–Retinoic Acid Receptor Oncoprotein," *Cell* 76:333–343 (1994).

Eyrolles, L., et al., "Retinoid Antagonists: Molecular Design Based on the Ligand Superfamily Concept," *Med. Chem. Res.* 2(6):361–367 (1992).

Fanjul, A., et al., "A new class of retinoids with selective inhibition of AP–1 inhibits proliferation," *Nature* 372:107–111 (1994).

Fanjul, A., et al., "Antiproliferative effects of a new class of retinoids with selective anti–AP–1 activity in various cancer cell lines," *Proc. Am. Assoc. Cancer Res.* 36:509, Abstract No. 3030 (1995).

Fisher, G.J., and Voorhees, J.J., "Molecular mechanisms of retinoid actions in skin," *FASEB J.* 10(9):1002–1013 (Jul. 1996).

Forman, B.M., et al., "Unique Response Pathways Are Established by Allosteric Interactions among Nuclear Hormone Receptors," *Cell* 81:541–550 (May 19, 1995).

Giguere, V., et al., "Identification of a receptor for the morphogen retinoic acid," *Nature* 330:624–629 (1987).

Giguère, V., "Retinoic Acid Receptors and Cellular Retinoid Binding Proteins: Complex Interplay in Retinoid Signaling," *Endocr. Rev.* 15(1):61–79 (1994).

Green, S., and Chambon, P., "Nuclear receptors enhance our understanding of transcription regulation," *Trends in Genetics* 4(11):309–314 (1988).

Grignani, F., et al., "The Acute Promyelocytic Leukemia–Specific PML–RARα Fusion Protein Inhibits Differentiation and Promotes Survival of Myeloid Precursor Cells," *Cell* 74:423–431 (1993).

Grignani, F., et al., "Acute Promyelocytic Leukemia: From Genetics to Treatment," *Blood* 83(1):10–25 (1994).

Gronemeyer, H., and Laudet, V., "Introduction: Nuclear Receptors," *Protein Profile* 2(11):1173–1180 (Feb. 1996).

Gudas, L.J., et al., "Cellular Biology and Biochemistry of the Retinoids," In: *The Retinoids: Biology, Chemistry, and Medicine,* 2nd Ed., Sporn, M.B., et al., eds., Raven Press, Ltd., New York, NY, pp. 443–520 (1994).

Guérin, E., et al., "Stromelysin–3 Induction and Interstitial Collagenase Repression by Retinoic Acid," *J. Biol. Chem.* 272:11088–11095 (1997).

Hembree, J.R., et al., "Retinoid X Receptor–specific Retinoids Inhibit the Ability of Retinoic Acid Receptor–specific Retinoids to Increase the Level of Insulin–like Growth Factor Binding Protein–3 in Human Ectocervical Epithelial Cells," *Cancer Res.* 56:1794–1799 (Apr. 1996).

Hong, W.K., et al., "13–cis–Retinoic Acid in the Treatment of Oral Leukoplakia," *New Engl. J. Med.* 315(24):1501–1505 (1986).

Hong, W.K., et al., "Prevention of Second Primary Tumors with Isotretinoin in Squamous–Cell Carcinoma of the Head and Neck," *New Engl. J. Med.* 323(12):795–801 (1990).

Horn, V., et al., "RAR and RXR selective ligands cooperatively induce apoptosis and neuronal differentiation in P19 embryonal carcinoma cells," *FASEB J. 10*:1071–1077 (Jul. 1996).

Jing, Y., et al., "Defective expression of cellular retinol binding protein type I and retinoic acid receptors α2, β2, and γ2 in human breast cancer cells," *FASEB J. 10*:1064–1070 (Jul. 1996).

Kastner, P., et al., "Structure, localization and transcriptional properties of two classes of retinoic acid receptor α fusion proteins in acute promyelocytic leukemia (APL): structural similarities with a new family of oncoproteins," *EMBO J. 11(2)*:629–642 (1992).

Kersten, S., et al., "Individual Subunits of Heterodimers Comprised of Retinoic Acid and Retinoid X Receptors Interact with Their Ligands Independently," *Biochem. 35*:3816–3824 (Mar. 1996).

Kishimoto, T., et al., "Interleukin–6 and Its Receptor: A Paradigm for Cytokines," *Science 258*:593–597 (1992).

Kleywegt, G.J., et al., "Crystal structures of cellular retinoic acid binding proteins I and II in complex with all–trans–retinoic acid and a synthetic retinoid," *Structure 2*:1241–1258 (1994).

Koken, M.H.M., et al., "The t(15;17) translocation alters a nuclear body in a retinoic acid–reversible fashion," *EMBO J. 13(5)*:1073–1083 (1994).

Kraemer, K.H., et al., "Prevention of Skin Cancer in Xeroderma Pigmentosum with the Use of Oral Isotretinoin," *New Engl. J. Med. 318(25)*:1633–1637 (1988).

Krężel, W., et al., "RXRγ null mice are apparently normal and compound RXRα$^{+/-}$ /RXRβ$^{-/-}$ /RXRγ$^{-/-}$ mutant mice are viable," *Proc. Natl. Acad. Sci. USA 93*:9010–9014 (Aug. 1996).

Krust, A., et al., "A third human retinoic acid receptor, hRAR–γ," *Proc. Natl. Acad. Sci. USA 86*:5310–5314 (1989).

Kurokawa, R., et al., "Regulation of retinoid signalling by receptor polarity and allosteric control of ligand binding," *Nature 371*:528–531 (1994).

Lanotte, M., et al., "NB4, a Maturation Inducible Cell Line With t(15;17) Marker Isolated From a Human Acute Promyelocytic Leukemia (M3)," *Blood 77(5)*:1080–1086 (1991).

Lavau, C., and Dejean, A., "The t(15;17) Translocation in Acute Promyelocytic Leukemia," *Leukemia 8(10)*:1615–1621 (1994).

Le Douarin, B., et al., "The N–terminal part of TIF1, a putative mediator of the ligand–dependent activation function (AF–2) of nuclear receptors, is fused to B–raf in the oncogenic protein T18," *EMBO J. 14(9)*:2020–2033 (May 1995).

Lehmann, J.M., et al., "Retinoids Selective for Retinoid X Receptor Response Pathways," *Science 258*:1944–1946 (1992).

Leid, M., et al., "Purification, Cloning, and RXR Identity of the HeLa Cell Factor with Which RAR or TR Heterodimerizes to Bind Target Sequences Efficiently," *Cell 68*:377–395 (1992).

Leid, M., et al., "Multiplicity generates diversity in the retinoic acid signalling pathways," *Trends in Biochem. Sci. 17*:427–433 (1992).

Leid, M., "Ligand–induced Alteration of the Protease Sensitivity of Retinoid X Receptor α," *J. Biol. Chem. 269(19)*:14175–14181 (1994).

Leng, X., et al., "Mouse Retinoid X Receptor Contains a Separable Ligand–Binding and Transactivation Domain in Its E Region," *Mol. Cell. Biol. 15(1)*:255–263 (Jan. 1995).

Lippman, S.M., et al., "13–cis–Retinoic Acid and Interferon α–2a: Effective Combination Therapy for Advanced Squamous Cell Carcinoma of the Skin," *J. Natl. Cancer Inst. 84(4)*:235–241 (1992).

Lippman, S.M., et al., "13–cis–Retinoic Acid Plus Interferon α2a: Highly Active Systemic Therapy for Squamous Cell Carcinoma of the Cervix," *J. Natl. Cancer Inst. 84(4)*:241–245 (1992).

Lo Coco, F., et al., "Molecular Evaluation of Response to All–Trans–Retinoic Acid Therapy in Patients With Acute Promyelocytic Leukemia," *Blood 77*:1657–1659 (1991).

Lotan, R., et al., "Enhanced Efficacy of Combinations of Retinoic Acid– and Retinoid X Receptor–selective Retinoids and α–Interferon in Inhibition of Cervical Carcinoma Cell Proliferation," *Cancer Res. 55*:232–236 (Jan. 15, 1995).

Lotan, R., "Retinoids in cancer chemoprevention," *FASEB J. 10*:1031–1039 (Jul. 1996).

Mangelsdorf, D.J., et al., "Nuclear receptor that identifies a novel retinoic acid response pathway," *Nature 345*:224–229 (1990).

Mangelsdorf, D.J., et al., "The Retinoid Receptors," In: *The Retinoids: Biology, Chemistry, and Medicine*, 2nd Ed., Sporn, M.B., et al., eds., Raven Press, Ltd., New York, NY, pp. 319–349 (1994).

Mangelsdorf, D.J., et al., "The Nuclear Receptor Superfamily: The Second Decade," *Cell 83*:835–839 (Dec. 15, 1995).

Mangelsdorf, D.J., and Evans, R.M., "The RXR Heterodimers and Orphan Receptors," *Cell 83*:841–850 (Dec. 15, 1995).

Meng–er, H., et al., "Use of All–Trans Retinoic Acid in the Treatment of Acute Promyelocytic Leukemia," *Blood 72(2)*:567–572 (1988).

Morriss–Kay, G.M., and Sokolova, N., "Embryonic development and pattern formation," *FASEB J. 10*:961–968 (Jul. 1996).

Mu, Z.–M., et al., "PML, a Growth Suppressor Disrupted in Acute Promyelocytic Leukemia," *Mol. Cell. Biol. 14(10)*:6858–6867 (1994).

Nagpal, S., et al., "RARs and RXRs: evidence for two autonomous transactivation functions (AF–1 and AF–2) and heterodimerization in vivo," *EMBO J. 12(6)*:2349–2360 (1993).

Nagpal, S., et al., "Separation of Transactivation and AP1 Antagonism of Retinoic Acid Receptor α," *J. Biol. Chem. 270*:923–927 (1995).

Nagy, L., et al., "Activation of Retinoid X Receptors Induces Apoptosis in HL–60 Cell Lines," *Mol. Cell. Biol. 15(7)*:3540–3551 (Jul. 1995).

Ostrowski, J., et al., "The N–terminal portion of domain E of retinoic acid receptors α and β is essential for the recognition of retinoic acid and various analogs," *Proc. Natl. Acad. Sci. USA 92*:1812–1816 (Mar. 1995).

Perez, A., et al., "PMLRAR homodimers: distinct DNA binding properties and heteromeric interactions with RXR," *EMBO J. 12(8)*:3171–3182 (1993).

Petkovich, M., et al., "A human retinoic acid receptor which belongs to the family of nuclear receptors," *Nature 330*:444–450 (1987).

Pfahl, M., "Nuclear Receptor/AP–1 Interaction," *Endocr. Rev. 14(5)*:651–658 (1993).

Roy, B., et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. Cell. Biol.* *15(12)*:6481–6487 (Dec. 1995).

Verma, A.K., "Inhibition of Both Stage I and Stage II Mouse Skin Tumor Promotion by Retinoic Acid and the Dependence of Inhibition of Tumor Promotion on the Duration of Retinoic Acid Treatment," *Cancer Res.* *47:*5097–5101 (1987).

Wang, Z.G., et al., "Role of PML in Cell Growth and the Retinoic Acid Pathway," *Science 279:*1547–1551 (1998).

Warrell, R.P., et al., "Differentiation Therapy of Acute Promyelocytic Leukemia with Tretinoin (All–Trans–Retinoic Acid)," *New Engl. J. Med. 324(20)*:1385–1393 (1991).

Warrell, R.P., et al., "Acute Promyelocytic Leukemia," *New Engl. J. Med. 329(3)*:177–189 (1993).

Weis, K., et al., "Retinoic Acid Regulates Aberrant Nuclear Localization of PML–RARα in Acute Promyelocytic Leukemia Cells," *Cell 76:*345–356 (1994).

Certificate of Correction for Document AA1, U.S. Patent No. 5,399,586, dated Jan. 13, 1996.

Certificate of Correction for Document AE1, U.S. Patent No. 5,780,676, dated Apr. 20, 1999.

* cited by examiner

| RETINOID | RAR | | |
|---|---|---|---|
| | α | β | γ |
| COMPOUND A | − | + | − |
| COMPOUND B | − | o | o |
| COMPOUND C | − | + | (+) |
| COMPOUND D | o | (+) | + |

FIG. 1

EtOH     1µM Cmpd. A     1µM SR 11237     1µM Cmpd. A + 1µM SR 11237
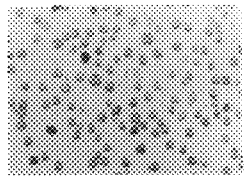 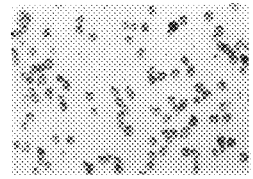 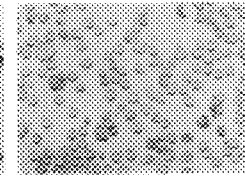 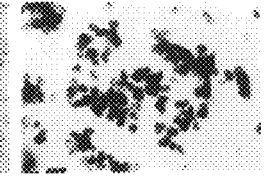
FIG.3A     FIG.3B     FIG.3C     FIG.3D
FIG.3E     FIG.3F     FIG.3G     FIG.3H
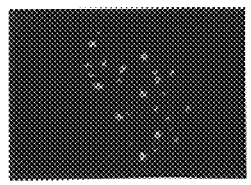 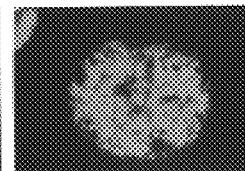 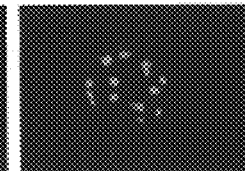 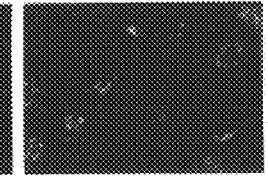
1nM Am80     1µM Cmpd. A     1µM Cmpd.A + 1µM SR 11237     1µM Cmpd. A + 1µM SR 11237

THERAPEUTIC COMBINATIONS OF RAR ANTAGONISTS AND RXR AGONISTS AND USE THEREOF

CROSS-REFERENCE TO RELATED APPLICATION

This application is a divisional of U.S. application Ser. No. 08/919,318, filed Aug. 28, 1997, which claims priority to U.S. Provisional Application No. 60/024,772, filed Aug. 28, 1996, the contents of which are fully incorporated by reference herein.

BACKGROUND OF THE INVENTION

1. Field of the Invention

The present invention relates to the fields of retinoid receptor biology and mammalian disease therapeutics. Specifically, the present invention provides compositions and methods for treating an animal, preferably a human, suffering from or predisposed to a physical disorder, by administering to the animal an effective amount of a composition comprising at least one RAR antagonist, preferably an RARα antagonist, and at least one RXR agonist.

2. Related Art

Retinoids

A number of studies have demonstrated that retinoids (vitamin A derivatives) are essential for normal growth, vision, tissue homeostasis, reproduction and overall survival (for reviews and references, See Sporn et al., *The Retinoids*, Vols. 1 and 2, Sporn et al., eds., Academic Press, Orlando, Fla. (1984)). For example, retinoids have been shown to be vital to the maintenance of skin homeostasis and barrier function in mammals (Fisher, G. J., and Voorhees, J. J., *FASEB J.* 10:1002–1013 (1996)). Retinoids are also apparently crucial during embryogenesis, since offspring of dams with vitamin A deficiency (VAD) exhibit a number of developmental defects (Wilson, J. G., et al., *Am. J. Anat.* 92:189–217 (1953); Morriss-Kay, G. M., and Sokolova, N., *FASEB J.* 10:961–968 (1996)). With the exceptions of those on vision (Wald, G., et al., *Science* 162:230–239 (1968)) and spermatogenesis in mammals (van Pelt, H. M. M., and De Rooij, D. G., *Endocrinology* 128:697–704 (1991)), most of the effects generated by VAD in animals and their fetuses can be prevented and/or reversed by retinoic acid (RA) administration (Wilson, J. G., et al.,*Am. J. Anat.* 92:189–217 (1953); Thompson etal., *Proc. Royal Soc.* 159:510–535 (1964); Morriss-Kay, G. M., and Sokolova, N., *FASEB J.* 10:961–968 (1996)). The dramatic teratogenic effects of maternal RA administration on mammalian embryos (Shenefelt, R. E., *Teratology* 5, 103–108 (1972); Kessel, M., *Development* 115:487–501 (1992); Creech Kraft, J., In *Retinoids in Normal Development and Teratogenesis*, G. M. Morriss-Kay, ed., Oxford University Press, Oxford, UK, pp. 267–280 (1992)), and the marked effects of topical administration of retinoids on embryonic development of vertebrates and limb regeneration in amphibians (Mohanty-Hejmadi et al., *Nature* 355:352–353 (1992); Tabin, C. J., *Cell* 66:199–217 (1991)), have contributed to the notion that RA may have critical roles in morphogenesis and organogenesis.

Retinoid Receptors

Except for those involved in visual perception (Wald, G. et al., *Science* 162:230–239 (1968)), the molecular mechanisms underlying the highly diverse effects of retinoids have until recently remained obscure. The discovery of nuclear receptors for RA (Petkovich et al., *Nature* 330:444–450 (1987); Giguère et al., *Nature* 330:624–629 (1987)) has greatly advanced the understanding of how the retinoids may exert their pleiotropic effects (Leid et al., *TIBS* 17:427–433 (1992); Linney, E., *Current Topics in Dev. Biol.* 27:309–350 (1992)). Since this discovery it has become apparent that the genetic activities of the RA signal are mediated through two families of receptors—the RAR family and the RXR family—which belong to the superfamily of ligand-inducible transcriptional regulatory factors that include steroid/thyroid hormone and vitamnin D3 receptors (for reviews see Leid et al., *TIBS* 17:427–433 (1992); Chambon, P., *Semin. Cell Biol.* 5:115–125 (1994); Chambon, P., *FASEB J.* 10:940–954 (1996); Giguere, V., *Endocrinol. Rev.* 15:61–79 (1994); Mangelsdorf, D. J., and Evans, R. M., *Cell* 83:841–850 (1995); Gronemeyer, H., and Laudet, V., *Protein Profile* 2:1173–1236 (1995)).

RAR Receptors

Receptors belonging to the RAR family (RARα, β and γ and their isoforms) are activated by both all-trans- and 9-cis-RA (Leid et al., *TIBS* 17:427–433 (1992); Chambon, P., *Semin. Cell Biol.* 5:115–125 (1994); Dollé, P., et al., *Mech. Dev.* 45:91–104 (1994); Chambon, P., *FASEB J.* 10:940–954 (1996)). Within a given species, the DNA binding (C) and the ligand binding (E) domains of the three RAR types are highly similar, whereas the C-terminal domain F and the middle domain D exhibit no or little similarity. The amino acid sequences of the three RAR types are also notably different in their B regions, and their main isoforms (α1 and α2, β1 to β1β4, and γ1 and γ2) further differ in their N-terminal A regions (Leid et al., *TIBS* 17:427–433 (1992)). Amino acid sequence comparisons have revealed that the interspecies conservation of a given RAR type is greater than the similarity found between the three RAR types within a given species (Leid et al., *TIBS* 17:427–433 (1992)). This interspecies conservation is particularly striking in the N-terminal A regions of the various RARα, β and γ isoforms, whose A region amino acid sequences are quite divergent. Taken together with the distinct spatio-temporal expression patterns observed for the transcripts of each RAR and RXR type in the developing embryo and in various adult mouse tissues (Zelent, A., et al., *Nature* 339:714–717 (1989); Dollé, P., et al., *Nature* 342:702–705 (1989); Dollé et al., *Development* 110:1133–1151 (1990); Ruberte et al., *Development* 108:213–222 (1990); Ruberte et al., *Development* 111:45–60 (1991), Mangelsdorf et al., *Genes & Dev.* 6:329–344 (1992)), this interspecies conservation has suggested that each RAR type (and isoform) may perform unique functions. This hypothesis is further supported by the finding that the various RAR isoforms contain two transcriptional activation functions (AFs) located in the N-terminal A/B region (AF-1) and in the C-terminal E region (AF-2), which can synergistically, and to some extent differentially, activate various RA-responsive promoters (Leid et al., *TIBS* 17:427–433 (1992); Nagpal, S., et al., *Cell* 70:1007–1019 (1992); Nagpal, S., et al., *EMBO J.* 12:2349–2360 (1993)).

RXR Receptors

Unlike the RARs, members of the retinoid X receptor family (RXRα, β and γ) are activated exclusively by 9cis-RA (Chambon, P., *FASEB J.* 10:940–954 (1996); Chambon, P., *Semin. Cell Biol.* 5:115–125 (1994); Dollé, P., et al., *Mech. Dev.* 45:91–104 (1994); Linney, E., *Current Topics in Dev. Biol.* 27:309–350 (1992); Leid et al., *TIBS* 17:427–433 (1992); Kastner et al., in *Vitamin A in Health and Disease*, R. Blomhoff, ed., Marcel Dekker, New York (1993)). However, the RXRs characterized to date are similar to the RARs in that the different RXR types also differ markedly in their N-terminal A/B regions (Leid et al., *TIBS* 17:427433 (1992); Leid et al., *Cell* 68:377–395 (1992); Mangelsdorf et al., *Genes and Dev.* 6:329–344 (1992)), and contain the same transcriptional activation functions in their N-terminal A/B region and C-terminal E region (Leid et al., *TIBS* 17:427–433 (1992); Nagpal, S., et al., *Cell* 70:1007–1019 (1992); Nagpal, S., et al., *EMBO J.* 12:2349–2360 (1993)).

RXRα and RXRβ have a widespread (possibly ubiquitous) expression pattern during mouse development and in the adult animal, being found in all fetal and adult tissues thus far examined (Mangelsdorf, D. J., et al., *Genes & Devel.* 6:329–344 (1992); Dollé, P., et al., *Mech. Devel.* 45:91–104 (1994); Nagata, T., et al., *Gene* 142:183–189 (1994)). RXRγ transcripts, however, appear to have a more restricted distribution, being expressed in developing skeletal muscle in the embryo (where their expression persists throughout life), in the heart (after birth), in sensory epithelia of the visual and auditory systems, in specific structures of the central nervous system, and in tissues involved in thyroid hormone homeostasis, e.g, the thyroid gland and thyrotrope cells in the pituitary (Mangelsdorf, D. J., et al., *Genes & Devel.* 6:329–344 (1992); Dollé, P., et al., *Mech. Devel.* 45:91–104 (1994); Sugawara, A., et al., *Endocrinology* 136:1766–1774 (1995); Liu, Q., and Linney, E., *Mol. Endocrinol.* 7:651–658 (1993)).

It is currently unclear whether all the molecular properties of RXRs characterized in vitro are relevant for their physiological functions in vivo. In particular, it is unknown under what conditions these receptors act as 9-cis-RA-dependent transcriptional regulators (Chambon, P., *Semin. Cell Biol.* 5:115–125 (1994)). The knock-outs of RXRα and RXRβ in the mouse have provided some insight into the physiological functions of these receptors. For example, the ocular and cardiac malformations observed in RXRα$^{-/-}$ fetuses (Kastner, P., et al., *Cell* 78:987–1003 (1994); Sucov, H. M., et al., *Genes & Devel.* 8:1007–1018 (1994)) are similar to those found in the fetal VAD syndrome, thus suggesting an important function of RXRα in the transduction of a retinoid signal during development. The involvement of RXRs in retinoid signaling is further supported by studies of compound RXRα/RAR mutants, which reveal defects that are either absent or less severe in the single mutants (Kastner, P., et al., *Cell* 78:987–1003 (1994); Kastner, P., et al., *Cell* 83:859–869 (1995)). Interestingly, however, knockout of RXRγ in the mouse induces no overt deleterious effects, and RXRγ$^{-/-}$ homozygotes which are also RXRα$^{-/-}$ or RXRβ$^{-/-}$ exhibit no additional abnormalities beyond those seen in RXRα$^{-/-}$, RXRβ$^{-/-}$ and fetal VAD syndrome fetuses (Krezel, W., et al., *Proc. Natl. Acad Sci. USA* 93(17):9010–9014 (1996)), suggesting that RXRγ, despite its highly tissue-specific expression pattern in the developing embryo, is dispensable for embryonic development and postnatal life in the mouse. The observation that live-born RXRγ$^{-/-}$/RXRβ$^{-/-}$/RXRα$^{+/-}$ mutants can grow to reach adult age (Krezel et al., *Proc. Natl. Acad Sci. USA* 93(17):9010–9014 (1996)) indicates that a single RXRα allele is sufficient to carry out all of the vital developmental and postnatal functions of the RXR family of receptors, particularly all of the developmental functions which depend on RARs and may require RXR partnership (Dollé, P., et al., *Mech. Dev.* 45:91–104 (1994); Kastner, P., et al., *Cell* 83:859–869 (1995)). Furthermore, the finding that RXRα$^{-/-}$/RXRγ$^{-/-}$ double mutant embryos are not more affected than are single RXRα$^{-/-}$ mutants (Krezel et al., *Proc. Natl. Acad. Sci. USA* 93(17):9010–9014 (1996)) clearly shows that RXRβ alone can also perform some of these functions. Therefore, the fact that RXRα alone and, to a certain extent RXRβ alone, are sufficient for the completion of a number of developmental RXR functions, clearly indicates the existence of a large degree of functional redundancy amongst RXRs. In this respect, the RXR situation is different from that of RARs, since all of types of RAR double mutants displayed much broader sets of defects than single mutants (Rowe, A., et al., *Develop.* 111:771–778 (1991); Lohnes, D., et al., *Develop.* 120:2723–2748 (1994); Mendelsohn, C., *Devlop.* 120:2749–2771 (1994)).

Retinoid Binding to RAR and RXR Receptors

The crystal structures of the ligand-binding domains (LBDs) of the RARs and RXRs have recently been elucidated (Bourget, W., et al., *Nature* 375:377–382 (1995); Renaud, J. P., et al., *Nature* 378:681–689 (1995); Wurtz, J. M., et al., *Nature Struct. Biol.* 3:87–94 (1996)). Among the various RAR types, substantial amino acid sequence identity is observed in these domains: comparison of the LBDs of RARα, RARβ and RARγ indicates that only three amino acid residues are variable in the ligand-binding pocket of these receptors. These residues apparently account for the fact that the various RAR types exhibit some selectivity in binding certain synthetic retinoids (Chen, J.-Y., et al., *EMBO J.* 14(6): 1187–1197 (1995); Renaud, J. P., et al., *Nature* 378:681–689 (1995)), and consideration of these divergent residues can be used to design RAR type-specific synthetic retinoids which may be agonistic or antagonistic (Chambon, P., *FASEB J.* 10:940–954 (1996)). This design approach may be extendable generally to other nuclear receptors, such as thyroid receptor a (Wagner, R. L., et al., *Nature* 378:690–697 (1995)), the ligand-binding pockets of which may chemically and structurally resemble those of the RARs (Chambon, P., *FASEB J.* 10:940–954 (1996)). Conversely, molecular modeling of the ligand-binding pocket of the RXRs demonstrates that there are no overt differences in amino acid composition between RXRα, RXRβ and RXRγ (Bourguet, W., et al., *Nature* 375:377–382 (1995); Wurtz, J. M., et al., *Nature Struct. Biol.* 3:87–94 (1996)), suggesting that design of type-specific synthetic ligands for the RXRs may be more difficult than for the RARs (Chambon, P., *FASEB J.* 10:940–954 (1996)).

Retinoid Signaling Through RAR:RXR Heterodimers

Nuclear receptors (NRs) are members of a superfamily of ligand-inducible transcriptional regulatory factors that include receptors for steroid hormones, thyroid hormones, vitamin D3 and retinoids (Leid, M., et al., *Trends Biochem. Sci.* 17:427–433 (1992); Leid, M., et al., *Cell* 68:377–395 (1992); and Linney, E. *Curr. Top. Dev. Biol.,* 27:309–350 (1992)). NRs exhibit a modular structure which reflects the existence of several autonomous functional domains. Based on amino acid sequence similarity between the chicken estrogen receptor, the human estrogen and glucocorticoid receptors, and the v-erb-A oncogene (Krust, A., et al., *EMBO J.* 5:891–897 (1986)), defined six regions—A, B, C, D, E and F—which display different degrees of evolutionary conservation amongst various members of the nuclear receptor superfamily. The highly conserved region C contains two zinc fingers and corresponds to the core of the DNA-binding domain (DBD), which is responsible for specific recognition of the cognate response elements. Region E is functionally complex, since in addition to the ligand-binding domain (LBD), it contains a ligand-dependent activation function (AF-2) and a dimerization interface. An autonomous transcriptional activation function (AF-1) is present in the non-conserved N-terminal A/B regions of the steroid receptors. Interestingly, both AF-1and AF-2 of steroid receptors exhibit differential transcriptional activation properties which appear to be both cell type and promoter context specific (Gronemeyer, H. *Annu. Rev. Genet* 25:89–123 (1991)).

As described above, the all-trans (T-RA) and 9-cis (9C-RA) retinoic acid signals are transduced by two families of nuclear receptors, RAR α, β and γ (and their isoforms) are activated by both T-RA and 9C-RA, whereas RXR α, β and γ are exclusively activated by 9C-RA (Allenby, G. et al., *Proc. Natl. Acad. Sci. USA* 90:30–34 (1993)). The three RAR types differ in their B regions, and their main isoforms (α1 and α2, β1–4, and γ1 and γ2) have different N-terminal A regions (Leid, M. et al., *Trends Biochem. Sci.* 17:427–433 (1992)). Similarly, the RXR types differ in their A/B regions (Mangelsdorf, D. J. et al., *Genes Dev.* 6:329–344 (1992)).

The E-region of RARs and RXRs has also been shown to contain a dimerization interface (Yu, V. C. et al., *Curr. Opin. Biotechnol.* 3:597–602 (1992)). Most interestingly, it was demonstrated that RAR/RXR heterodimers bind much more efficiently in vitro than homodimers of either receptor to a number of RA response elements (RAREs) (Yu, V. C. et al., *Cell* 67:1251–1266 (1991); Berrodin, T. J. et al., *Mol. Endocrinol* 6:1468–1478 (1992); Bugge, T. H. et al., *EMBO J.* 11:1409–1418 (1992); Hall, R. K. et al., *Mol. Cell. Biol.* 12:5527–5535 (1992); Hallenbeck, P. L. et al., *Proc. Natl. Acad. Sci. USA* 89:5572–5576 (1992); Husmann, M. et al., *Biochem. Biophys. Res. Commun.* 187:1558–1564 (1992); Kliewer, S. A. et al., *Nature* 355:446–449 (1992); Leid, M. et al., *Cell* 68:377–395 (1992); Marks, M. S. et al., *EMBO J.* 11:1419–1435 (1992); Zhang, X. K. et al., *Nature* 355:441–446 (1992)). RAR and RXR heterodimers are also preferentially formed in solution in vitro (Yu, V. C. et al., *Cell* 67:1251–1266 (1991); Leid, M. et al., *Cell* 68:377–395 (1992); Marks, M. S. et al., *EMBO J.* 11:1419–1435 (1992)), although the addition of 9C-RA appears to enhance the formation of RXR homodimers in vitro (Lehman, J. M. et al., *Science* 258:1944–1946 (1992); Zhang, X. K. et al., *Nature* 358:587–591 (1992b)).

It has been shown that activation of RA-responsive promoters likely occurs through RAR:RXR heterodimers rather than through homodimers (Yu, V. C. et al., *Cell* 67:1251–1266 (1991); Leid et al., *Cell* 68:377–395 (1992b); Durand et al., *Cell* 71:73–85 (1992); Nagpal et al., *Cell* 70:1007–1019 (1992); Zhang, X. K. et al., *Nature* 355, 441–446 (1992); Kliewer et al., *Nature* 355:446–449 (1992); Bugge et al., *EMBO J.* 11:1409–1418 (1992); Marks et al., *EMBO J.* 11:1419–1435 (1992); Yu, V. C. et al., *Cur. Op. Biotech.* 3:597–602 (1992); Leid et al., *TIBS* 17:427–433 (1992); Laudet and Stehelin, *Curr. Biol.* 2:293–295 (1992); Green, S., *Nature* 361:590–591 (1993)). The RXR portion of these heterodimers has been proposed to be silent in retinoid-induced signaling (Kurokawa, R., et al., *Nature* 371:528–531 (1994); Forman, B. M., et al., *Cell* 81:541–550 (1995); Mangelsdorf, D. J., and Evans, R. M., *Cell* 83:835–850 (1995)), although conflicting results have been reported on this issue (Apfel, C. M., et al., *J. Biol. Chem.* 270(51):30765–30772 (1995); see Chambon, P., *FASEB J.* 10:940–954 (1996) for review). Although the results of these studies strongly suggest that RAR/RXR heterodimers are indeed functional units that transduce the RA signal in vivo, it is unclear whether all of the suggested heterodimeric combinations occur in vivo (Chambon, P., *Semin. Cell Biol.* 5:115–125 (1994)). Thus, the basis for the highly pleiotropic effect of retinoids may reside, at least in part, in the control of different subsets of retinoid-responsive promoters by cell-specifically expressed heterodimeric combinations of RAR:RXR types (and isoforms), whose activity may be in turn regulated by cell-specific levels of all-trans- and 9-cis-RA (Leid et al., *TIBS* 17:427–433 (1992)).

The RXR receptors may also be involved in RA-independent signaling. For example, the observation of aberrant lipid metabolism in the Sertoli cells of RXRβ$^{-/-}$ mutant animals suggests that functional interactions may also occur between RXRβ and the peroxisomal proliferator-activated receptor signaling pathway (WO 94/26100; Kastner, P., et al., *Genes & Devel.* 10:80–92 (1996)).

Therapeutic Uses of Retinoids

Overview

As retinoic acid is known to regulate the proliferative and differentiative capacities of several mammalian cell types (Gudas, L. J., et al., In *The Retinoids*, 2nd ed., Sporn, M. B., et al., eds., New York: Raven Press, pp. 443–520 (1994)), retinoids are used in a variety of chemopreventive and chemotherapeutic settings. The prevention of oral, skin and head and neck cancers in patients at risk for these tumors has been reported (Hong, W. K. et al., *N. Engl. J. Med.* 315:1501–1505 (1986); Hong, W. K. et al., *N. Engl. J. Med.* 323:795–801 (1990); Kraemer, K. H. et al., *N. Engl. J. Med.* 318:1633–1637 (1988); Bollag, W. et al., *Ann. Oncol.* 3:513–526 (1992); Chiesa, F. et al., *Eur. J. Cancer B. Oral Oncol.* 28:97–102 (1992); Costa, A. et al., *Cancer Res.* 54:Suppl. 7, 2032–2037 (1994)). Retinoids have also been used to treat squamous cell carcinoma of the cervix and the skin (Verma, A. K., *Cancer Res.* 47:5097–5101 (1987); Lippman S. M. et al., *J. Natl Cancer Inst.* 84:235–241 (1992); Lippman S. M. et al., *J. Natl Cancer Inst.* 84:241–245 (1992)) and Kaposi's sarcoma (Bonhomme, L. et al., *Ann. Oncol.* 2:234–235 (1991)), and have found significant use in the therapy of acute promyelocytic leukemia (Huang, M. E. et al., *Blood* 72:567–572 (1988); Castaigne, S. et al., *Blood* 76:1704–1709 (1990); Chomienne, C. et al., *Blood* 76:1710–1717 (1990); Chomienne, C. et al., *J. Clin. Invest.* 88:2150–2154 (1991); Chen Z. et al., *Leukemia* 5:288–292 (1991); Lo Coco, F. et al., *Blood* 77:1657–1659 (1991); Warrell, R. P., et al., *N. Engl. J. Med.* 324:1385–1393 (1991); Chomienne, C., et al., *FASEB J.* 10:1025–1030 (1996)).

Acute Promyelocytic Leukemia (APL)

A balanced chromosomal translocation, t(15;17), has been identified in most acute promyelocytic leukemia (APL) cells (Larson, A. R., et al., *Am. J. Med.* 76:827–841 (1984)). The breakpoint for this translocation occurs within the second intron of the RARα gene (Alcalay, M. D., et al., *Proc. Natl. Acad Sci. USA* 88:1977–1981 (1991); Chang, K. S., et al., *Leukemia* 5:200–204 (1991); Chen, S., et al., *Blood* 78:2696–2701 (1991) and within two loci of the gene encoding the putative zinc finger transcription factor PML (Goddard, A., et al., *Science* 254:1371–1374(1991)). This reciprocal t(15;17) translocation leads to the generation of a PML-RARα fusion protein which is co-expressed with PML and RARα in APL cells (for reviews and references, see Warrell, R. P., et al., *N. Engl. J. Med.* 329:177–189 (1993); Grignani, F., et al., *Blood* 83:10–25 (1994); Lavau, C., and Dejean, A., *Leukemia* 8:1615–1621 (1994); de Thé, H., *FASEB J.* 10:955–960 (1996)). The PML-RARα fusion is apparently responsible for the differentiation block at the promyelocytic stage, since (i) it is observed in nearly all APL patients (Warrell, R. P., et al., *N. Engl. J. Med.* 329:177–189 (1993); Grignáni, F., et at, *Blood* 83:10–25 (1994); Lavau, C., and Dejean, A., *Leukemia* 8:1615–1621 (1994)), (ii) it inhibits myeloid differentiation when overexpressed in U937 or HL60 myeloblastic leukemia cells (Grignani, F., et al., *Cell* 74:423–431 (1993)), and (iii) complete clinical remission due to differentiation of the leukemic cells to mature granulocytes upon treatment with all-trans retinoic acid (T-RA) is tightly linked to PML-RARα expression (Warrell, R. P., et al., *N. Engl. J. Med.* 324:1385–1393 (1991); Lo Coco, R., et al., *Blood* 77:1657–1659 (1991);

Chomienne, C., et al., *FASEB J.* 10:1025–1030 (1996)). Multiple studies have addressed the possible impact of PML-RARα fusion protein formation on cell proliferation (Mu, X. M., et al., Mol. Cell. Biol. 14:6858–6867 (1994)) and apoptosis (Grignani, F., et al., *Cell* 74:423–431 (1993)), APP1 transrepression (Doucas, V., et al., *Proc. Natl. Acad Sci. USA* 90:9345–9349 (1993)), and vitamin D3 signaling (Perez, A., et al., *EMBO J.* 12:3171–3182 (1993)), but the mechanism(s) by which PML-RARα blocks myeloid cell maturation has remained elusive. Consistent with the aberrant nuclear compartmentalization of PML-RARα, which adopts the "PML-type" location upon RA treatment (Dyck, J. A., et al., *Cell* 76:333–343 (1994); Weis, K., et al., *Cell* 76:345–358 (1994); Koken, M. H., et al., *EMBO J.* 13:1073–1083 (1994)), the currently prevailing hypothesis is that PML-RARα possesses altered transcriptional properties compared to PML or RARα and/or may act in a dominant-negative manner (Perez, A., et al., *EMBO J.* 12:3171–3182 (1993); de Theé, H., et al., *Cell* 66:675–684 (1991); Kastner, P., et al., *EMBO J.* 11:629–642 (1992)).

SUMMARY OF THE INVENTION

By the invention, a method is provided for treating an animal, preferably a human, suffering from or predisposed to a physical disorder. The method comprises administering to the animal an effective amount of a composition comprising at least one RAR antagonist, preferably an RARα antagonist, and most preferably Compound A or Compound B, and at least one RXR agonist, most preferably SR11237. The combination of an RXR agonist, which has no therapeutic effects alone, with an RAR antagonist allows the use of lower doses of the RAR antagonist than were previously thought to be efficacious; this approach obviates many of the undesirable physiological side-effects of treatment with RAR antagonists. Physical disorders treatable by the method of the present invention include cancers (preferably a skin cancer, an oral cavity cancer, a lung cancer, a mammary gland cancer, a prostatic cancer, a bladder cancer, a liver cancer, a pancreatic cancer, a cervical cancer, an ovarian cancer, a head and neck cancer, a colon cancer, a germ cell cancer such as a teratocarcinoma or a leukemia, and most preferably acute promyelocytic leukemia), a skin disorder (preferably psoriasis, actinic keratosis, acne, ichthyosis, photoaging or corticosteroid-induced skin atrophy), rheumatoid arthritis and a premalignant lesion.

The invention also provides pharmaceutical compositions comprising at least one RAR antagonist which is preferably an RARα antagonist and most preferably Compound A or Compound B, at least one RXR agonist which is most preferably SR11237, and a pharmaceutically acceptable carrier or excipient therefor. The invention further encompasses the use of these pharmaceutical compositions in treating an animal, preferably a human, that is suffering from or is predisposed to a physical disorder. Physical disorders treatable using the pharmaceutical compositions of the present invention include those described above.

Other preferred embodiments of the present invention will be apparent to one of ordinary skill in light of the following drawings and description of the invention, and of the claims.

BRIEF DESCRIPTION OF THE DRAWINGS

FIG. 1. Summary of agonistic and antagonistic activities of the various BMS synthetic retinoids. "+" indicates agonistic for the given receptor, "(+)" weakly agonistic, "−" antagonistic and "0" no activity.

FIGS. 3A–3H. Synergy between RARα agonists or antagonists and RXR agonists for the induction of NB4 cell differentiation. Photomicrographs of cells stained with nitroblue tetrazolium (a–d) or immunofluorescence photomicrographs of cells stained with anti-PML antisera (e–h) after treatment for 4 days with ethanol or the indicated retinoid(s).

DETAILED DESCRIPTION OF THE INVENTION

Figure 2:
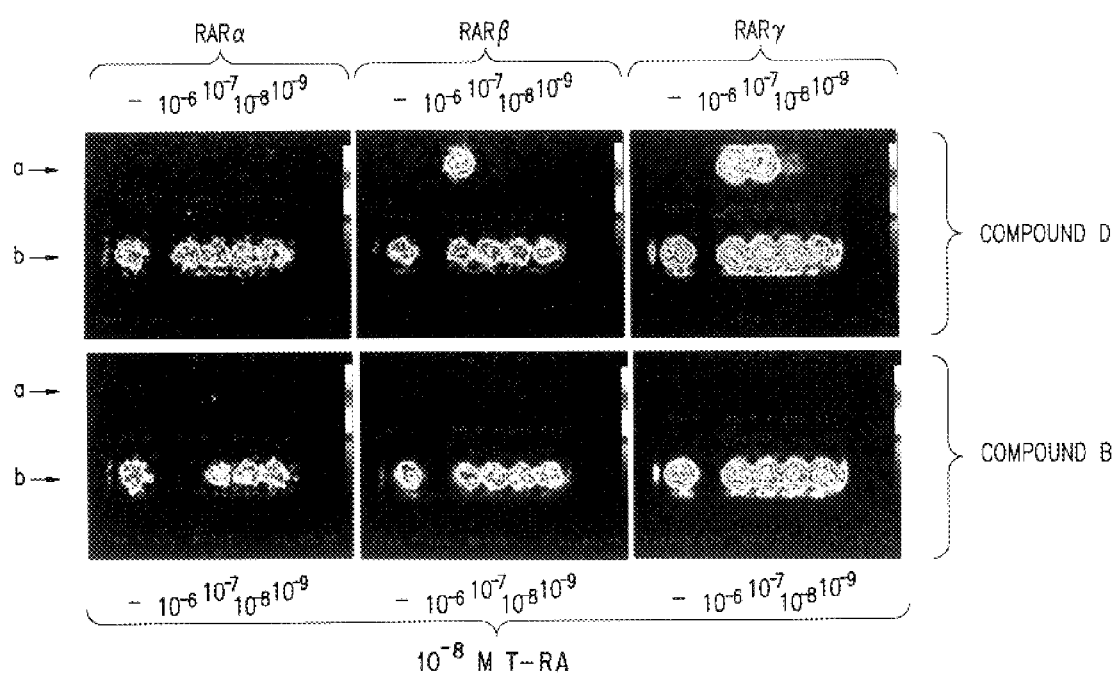
FIG. 2. False color representation of single photon camera-analysis of retinoid-induced luciferase activity originating in HeLa reporter cells treated with RAR-specific ligands alone (lane a), or with 10 nM all-trans-RA (lane b).

Synthesis of RAR and RXR Agonists and Antagonists

The agents to be used in the methods of the present invention can be, but are not limited to, peptides, carbohydrates, steroids and vitamin derivatives, which may each be natural or synthetic (prepared, for example, using methods of synthetic organic and inorganic chemistry that are well-known in the art). According to the invention, the agents can be selected and screened at random. For random screening, agents such as peptides, carbohydrates, steroids or vitamin derivatives (e.g., derivatives of RA) are selected at random and are assayed, using direct or indirect methods that are routine in the art, for their ability to bind to a RAR or RXR receptor or a functional retinoid RAR:RXR receptor heterodimer. For example, candidate RAR agonists according to the present invention include synthetic retinoids such as Am580, Compound 1 and Compound 2 (the structures of which are disclosed in Ostrowski et al., *Proc. Natl. Acad Sci. USA* 92:1812–1816 (1995), which is incorporated by reference herein in its entirety) and Am80 (Roy et al., *Mol. Cell. Biol.* 15(12):6481–6487 (1995), which is incorporated by reference herein in its entirety). Candidate RXR agonists according to the present invention include synthetic retinoids such as SR11237 (the structure of which is disclosed in Lehman, J. M., et al., *Science* 258:1944–1946 (1992), which is incorporated herein in its entirety). Candidate RAR antagonists include, but are not limited to, those described previously (Chen et al., *EMBO J.* 14:1187–1197 (1995); Roy et al., *Mol. Cell. Biol.* 15(12):6481–6487 (1995); Chen et al., *EMBO J.* 14:1187–1197 (1995), each of which is incorporated by reference herein in their entireties), and Compound A and Compound B as described in detail below, Thus, methods are known in the art for developing candidate RAR antagonists and RXR agonists, for screening as described below, to be used according to the present invention. Specifically, the invention can be carried out with the RAR antagonist compounds designated herein as "Compound A" and "Compound B," which respectively have the following structures:

Compound A

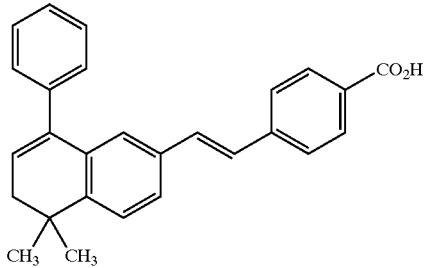

Compound B

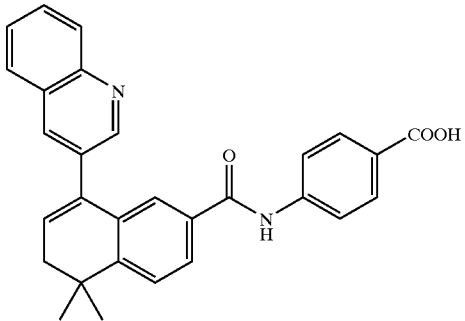

These compounds may be prepared as described in U.S. Pat. No. 5,559,248, which is incorporated herein by reference in its entirety. Other useful RAR antagonists are described in, for example, Eyrolles et al., *Med. Chem. Res.* 2:361–367 (1992) and Apfel et al., *Proc. Natl. Acad. Sci. USA* 89:7129–7133 (1992), which are incorporated by reference herein in their entireties. The invention can also be carried out with the RXR agonist LG1069, the structure and preparation of which are described in Boehm et al., *J. Med. Chem.* 37:2930–2941 (1994), which is incorporated by reference herein in its entirety. Other useful RXR agonists are described in, for example, Lehmann et al., *Science* 258:1944–1946 (1992), which is incorporated by reference herein in its entirety. Other RAR antagonists and RXR agonists suitable for use in the present invention may be prepared by the above-cited methods and others routine to those of ordinary skill in the art.

Screening Methods

A number of methods for screening candidate RAR antagonists and RXR agonists, generated by rational design or computer modeling as described above, are well-known in the art, and will allow one of ordinary skill to determine if a compound is useful in the methods of the present invention. For example, in Chen et al., *EMBO J.* 14(6):1187–1197 (1995), three 'reporter' cell lines have been used to characterize a number of RARα-, RARβ-, or RARγ-specific dissociating synthetic retinoids that selectively induce the AF-2 activation function present in the LBD of RARβ (βAF-2) (Chen, J.-Y., et al., *EMBO J.* 14(6):1187–1197 (1995)). These cell lines stably express chimeric proteins containing the DNA binding domain of the yeast transactivator GAL4 fused to the EF regions (which contain that LBD and the AF-2 activation function) of RARα (GAL-RARα), RARβ (GAL-RARβ) or RARγ (GAL-RARγ), and a luciferase reporter gene driven by a pentamer of the GAL4 recognition sequence ('17 m') in front of the β-globin promoter (17 m)5-GAL-Luc). In these cell lines, the RAR ligands thus induce luciferase activity that can be measured in the intact cells using a single-photon-counting camera. This reporter system is insensitive to endogenous receptors which cannot recognize the GAL4 binding site. Using analogous screening assays, these synthetic retinoids, like RA, have been reported to inhibit the anchorage-independent growth of oncogene-transformed 3T3 cells, while the promoter of the human interleukin-6 (IL-6) gene, whose product is involved in the regulation of hematopoiesis, immune responses and inflammation (Kishimoto, T. et al., *Science* 258:593–597 (1992)), has been shown to be induced by RA but not by the synthetic dissociating retinoids which repressed its activity. In a similar manner, RXR agonists have been identified using cell lines that express a RXR receptor linked to a TREpal-tk reporter gene which is activated by both RAR-RXR heterodimers and RXR homodimers (Lehmann, J. M., et al., *Science* 258:1944–1946 (1992)). Thus, reporter cell lines that are easily constructed, by methods routine to one of ordinary skill, may be used to distinguish not only the specific RAR or RXR types to which a candidate ligand will bind, but also whether that binding induces an activating (i.e., agonistic) or repressive (i.e., antagonistic) effect. Although the above-referenced reporter cell lines comprised the luciferase or thymidine kinase genes as reporters, other reporters such as Neo, CAT, β-galactosidase or Green Fluorescent Protein are well known in the art and may be used in a similar fashion to carry out the present invention. For example, references disclosing reporter plasmids containing a reporter gene and expression vectors encoding a LBD of a nuclear receptor include Meyer et al., *Cell* 57:433–442 (1989); Meyer et al., *EMBO J.* 9(12):3923–3932 (1990); Tasset et al., *Cell* 62:1177–1187 (1990); Gronemeyer, H., and Laudet, V., *Protein Profile* 2:1173–1308 (1995); Webster et al., *Cell* 54:199–207 (1988); Strähle et al., *EMBO J.* 7:3389–3395 (1988); Seipel et al., *EMBO J.* 11:4961–4968 (1992); and Nagpal et al., *EMBO J.* 12:2349–2360(1993).

Other routine assays have been used to screen compounds for their agonistic or antagonistic properties on functions of other nuclear receptors, such as steroid receptors. For example, a transient expression/gel retardation system has been used to study the effects of the synthetic steroids RU486 and R5020 on glucocorticoid and progesterone receptor function (Meyer, M-E., et al., *EMBO J.* 9(12):3923–3932 (1990)). Similar assays have been used to show that tamoxifen competitively inhibits estradiol-induced ERAP160 binding to the estrogen receptor, suggesting a mechanism for its growth-inhibitory effects in breast cancer (Halachimi, S., et al., *Science* 264:1455–1458 (1994)). Since the RAR and RXR receptors are apparently structurally similar to other nuclear receptors such as the steroid receptors (as reviewed in Chambon, P., *FASEB J.* 10:940–954 (1996)), routine assays of this type may be useful in assessing compounds for their agonistic or antagonistic activities on RAR or RXR receptors.

As an alternative routine method, the effect of a candidate agonist or antagonist on the binding of the ligand-dependent AF-2 modulator TIF1 to a RAR or RXR LBD can be studied using glutathione-S-transferase (GST) interaction assays by tagging the LBDs with GST as described in detail in Le Douarin et al., *EMBO J* 14:2020–2033 (1995).

In another screening assay, transgenic mice and cell lines that are altered in their expression of one or more RAR or RXR receptors may be made as described previously (Krezel, W., et al., *Proc. Natl. Acad. Sci. USA* 93(17):9010–9014 (1996)) and may be used to identify agonists and antagonists of specific members of the RAR/RXR class of receptors using methods described previously (WO 94/26100). In such an assay, the agent which is to be tested will be incubated with one or more of the transgenic cell lines or mice or tissues derived therefrom. The level of binding of the agent is then determined, or the effect the agent has on development or gene expression is monitored, by techniques that are routine to those of ordinary skill. As used herein, the term "incubate" is defined as contacting the compound or agent under investigation with the appropriate cell or tissue, or administering the agent or compound to the appropriate mouse, via any one of the well-known routes of administration including enteral, intravenous, subcutaneous, and intramuscular.

Other assays, such as those described in detail below in Examples 1 and 2, may also be used to determine the agonistic or antagonistic effects of RAR and RXR ligands. For example, certain agonistic retinoids will induce the association of endogenous PML/PML-RARα fusion protein with nuclear bodies in cells from APL patients (Dyck, J. A., et al., *Cell* 76:333–343 (1994); Weis, K., et al., *Cell* 76:345–356 (1994); Koken, M. H. M., et al., *EMBO J.* 13(5):1073–1083 (1994)) or in related established cell lines such as NB4 (Lanotte, M., et al., *Blood* 77(5):1080–1086 (1991)). These effects of RAR or RXR agonists or antagonists may be determined, for example, by various immunological techniques such as immunofluorescent or immunoelectron microscopy, using antibodies specific for PML, RAR and/or PML-RARα fusion proteins. RAR or RXR agonists or antagonists may also be identified by their abilities to induce the in vitro differentiation (maturation) of certain established cell lines such as HL-60 myeloblastic leukemia cells (Nagy, L., et al., *Mol. Cell. Biol.* 15(7):3540–3551 (1995)), NB4 promyelocytic cells (Lanotte, M., et al., *Blood* 77(5):1080–1086 (1991), P19 or F9 embryonic carcinoma cells (Roy, B., et al., *Mol. Cell. Biol.* 15(12):6481–6487 (1995); Horn, V., et al., *FASEB J.* 10:1071–1077 (1996)), or ras-transformed 3T3 cells (Chen et al., *EMBO J.* 14(6):1187–1197 (1995)). Ligand-induced differentiation in these and other cell lines may be determined by assaying ligand-treated or -untreated cells for the expression of a variety of well-known markers of differentiation as generally described in the above references.

Similarly, the candidate antagonists or agonists may be screened by measuring their abilities to induce apoptosis (programmed cell death) in, for example, HL60 cells (Nagy, L., et al., *Mol. Cell. Biol.* 15(7):3540–3551 (1995)) or P19 cells (Horn, V., et al., *FASEB J.* 10:1071–1077 (1996)), or in other primary cells or established cell lines. Apoptosis is typically assessed by measurement of ligand-induced DNA fragmentation, which is accomplished by methods such as gel electrophoresis (appearance of smaller molecular weight bands), microscopy (changes in plasma membrane morphology such as formation of surface protruberances ("blebbing") or in nuclear morphology such as pycnosis or fragmentation) or expression of the putative apoptosis suppressive protein BCL-2 (decreased in apoptotic cells); for general methods and discussions of these assays as they pertain to RAR and RXR biology, see Nagy, L., et al., *Mol. Cell. Biol.* 15(7):3540–3551 (1995); Horn, V., et al., *FASEB J.* 10:1071–1077 (1996)). Other methods for assaying ligand-induced apoptosis in primary cells and established cell lines, such as flow cytometry or particle analysis (appearance of smaller particles with different light scatter and/or DNA content profiles), are well-known in the art (Telford, W. G., et al., *J. Immunol. Meth.* 172(1):1–16 (1994); Campana, D., et al., *Cytometry* 18(2):68–74 (1994); Sgonc, R., and Wick, G., *Int. Arch. Allergy Immunol.* 105 (4):327–332 (1994); Fraker, P. J., et al., *Meth. Cell Biol.* 46:57–76 (1995); Sherwood, S. W., and Schimke, R. T., *Meth. Cell Biol.* 46:77–97 (1995); Carbonari, M., et al., *Cytometry* 22(3):161–167 (1995); Mastrangelo, A. J., and Betenbaugh, M. J., *Curr. Opin. Biotechnol.* 6(2):198–202 (1995)). Finally, screening of agonists or antagonists may be accomplished by an assay known as "in vivo footprinting" (Mueller, P. R., and Wold, B., *Science* 246:780–786 (1989); Garrity, P. A., and Wold, B. J., *Proc. Natl. Acad. Sci. USA* 89:1021–1025 (1992)), as described in more detail below in Examples 1 and 2, which has proven useful for analysis of RA-induced transcription of RARβ2 (Dey, A., et al., *Mol. Cell. Biol.* 14(12):8191–8201 (1994)).

Other methods for determining the agonistic or antagonistic activities of a candidate ligand which are routine in the art may also be used in carrying out the present invention. In performing such assays, one skilled in the art will be able to determine which RAR or RXR receptor type an agent binds to, what specific receptor(s) are utilized by a given compound, and whether the agent is an agonist or antagonist of the given receptor(s).

Clinical Indications

Thus, methods for identifying, synthesizing and screening RAR antagonists and RXR agonists are well-known in the art. These ligands may then be used according to the present invention in the treatment of a variety of physical disorders in animals, particularly mammals including humans. As described above, retinoic acid is known to regulate the proliferative and differentiative capacities of several mammalian cell types (Gudas, L. J. et al. (1994) In Sporn, M. B., Roberts, A. B. and Goodman, D. S.(eds), *The Retinoids*. 2nd edition, Raven Press, New York, pp. 443–520). Retinoids have thus been used in a number of chemopreventive and chemotherapeutic regimens. Included among these clinical approaches are the prevention and/or treatment of a variety of cancers and premalignant lesions thereof, such as those of the oral cavity, skin (including squamous cell carcinoma, melanoma and Kaposi's sarcoma), head and neck, cervix, ovary, lung, mammary gland, bladder, prostate, liver and pancreas (Hong, W. K., et al., *N. Engl. J. Med.* 315:1501–1505 (1986); Verma, A. K., *Cancer Res.* 47:5097–5101 (1987); Hong, W. K., et al., *N. Engl. J. Med.* 323:795–801 (1990); Kraemer, K. H., et al., *N. Engl. J. Med.* 318:1633–1637 (1988); Bonhomme, L., et al., *Ann. Oncol.* 2:234–235 (1991); Bollag, W., et al.,*Ann. Oncol.* 3:513–526 (1992); Chiesa, F., et al., *Eur. J. Cancer B. Oral Oncol.* 28:97–102 (1992); Lippman, S. M., et al., *J. Natl Cancer Inst.* 84:235–241 (1992); Lippman, S. M., et al., *J. Natl Cancer Inst.* 84:241–245 (1992); Costa, A., et al., *Cancer Res.* 54(Suppl. 7): 2032–2037 (1994); de Thé, H., *FASEB J.* 10:955–960 (1996); Lotan, R., *FASEB J.* 10:1031–1039 (1996); Bérard, J., et al., *FASEB J.* 10:1091–1097 (1996)). More specifically, retinoids have been used to treat patients afflicted with certain leukemias, particularly acute promyelocytic leukemia (Huang, M. E., et al., *Blood* 72:567–572 (1988); Castaigne, S., et al., *Blood* 76:1704–1709 (1990); Chomienne, C., et al., *Blood* 76:1710–1717 (1990); Chomienne, C., et al.,*J. Clin. Invest.* 88:2150–2154 (1991);

Chen, Z., et al., *Leukemia* 5:288–292 (1991); Lo Coco, F., et al., *Blood* 77:165701659 (1991); Warrel, R. P., et al., *N. Engl. J. Med.* 324:1385–1393 (1991); Chomienne, C., et al., *FASEB J.* 10:1025–1030 (1996)). Retinoids have also proven effective in the treatment of certain skin disorders such as psoriasis, acne, ichthyosis, photoaging and corticosteroid-induced skin atrophy such as that which may accompany the topical use of corticosteroids in treating inflammation of the skin (Fisher, G. J., and Voorhees, J. J., *FASEB J.* 10:1002–1013 (1996)).

Thus, the combinations of RAR antagonists and RXR agonists of the present invention may be used in the treatment of an animal, preferably a mammal including a human, that is suffering from or is predisposed to a variety of physical disorders. As used herein, an animal that is "predisposed to" a physical disorder is defined as an animal that does not exhibit a plurality of overt physical symptoms of the disorder but that is genetically, physiologically or otherwise at risk for developing the disorder. The combinations of RAR antagonists and RXR agonists may thus be used prophylactically as chemopreventive agents for such disorders. In treating the animal with the combinations of the present invention, the RXR agonist may be administered to the animal prior to, concurrently with, or following administration of the RAR antagonist.

Physical disorders treatable with the combinations and methods of the present invention include a variety of cancers, such as skin cancer (including melanoma and Kaposi's Sarcoma), oral cavity cancer, lung cancer, mammary gland cancer, prostatic cancer, bladder cancer, liver cancer, pancreatic cancer, cervical cancer, ovarian cancer, head and neck cancer, colon cancer, germ cell cancer (including teratocarcinoma) and leukemia, most preferably acute promyelocytic leukemia. Other physical disorders treatable with the combinations and methods of the present invention include skin disorders such as psoriasis, actinic keratosis, acne, ichthyosis, photoaging and corticosteroid-induced skin atrophy, and rheumatoid arthritis. The compositions and methods of the present invention may also be used in the prevention of disease progression, such as in chemoprevention of the progression of a premalignant lesion to a malignant lesion. The compositions and methods of the present invention may also be used to treat an animal suffering from, or predisposed to, other physical disorders that respond to treatment with retinoids.

Formulation and Methods of Administration

As indicated above, RAR- and RXR-selective ligands are known to elicit a wide array of cellular responses, several of which have clinical applications in treating a patient. The term "patient" as used herein is defined as an animal, preferably a mammal, including a human. By the invention, the dose of one or more RAR antagonists can be significantly reduced when co-administered with at least one RXR agonist. As used herein, "an effective amount of a RAR (or RXR) antagonist" is defined as an amount effective to elicit a cellular response in cells which express a RAR (or RXR) receptor. Example clinical therapies which involve administering compositions comprising at least one RAR antagonist and at least one RXR agonist to a patient are discussed in more detail below.

Combinations of RAR agonists and RXR agonists with potential use in human therapy are known in the art (Lehmann, J. M., et al., *Science* 258:1944–1946 (1992); Durand, B., et al., *EMBO J.* 13:5370–5382 (1994); Lotan, R., et al., *Cancer Res.* 55:232–236 (1995); Roy, B., et al., *Mol. Cell. Biol.* 15(12):6481–6487 (1995); Horn, V., et al., *FASEB J.* 10:1071–1077 (1996)). None of these previous disclosures, however, described or predicted the unexpected finding of the current invention that combinations of RAR antagonists with RXR agonists are useful in treating a variety of physical disorders.

Pharmaceutical compositions are thus provided comprising at least one RAR antagonist (such as those described above), at least one RXR agonist (such as those described above), and a pharmaceutically acceptable carrier or excipient, which may be administered orally, rectally, parenterally, intrasystemically, intravaginally, intraperitoneally, topically (as by powders, ointments, drops or transdermal patch), bucally, or as an oral or nasal spray. Importantly, by co-administering a RAR antagonist and a RXR agonist, clinical side effects can be reduced by using lower doses of both the RAR antagonist and the RXR agonist. As indicated, it will be understood that the RXR agonist can be "co-administered" either before, after, or simultaneously with the RAR antagonist, depending on the exigencies of a particular therapeutic application. By "pharmaceutically acceptable carrier" is meant a non-toxic solid, semisolid or liquid filler, diluent, encapsulating material or formulation auxiliaiy of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 $\mu$m in diameter. Suitable inert carriers include sugars such as lactose. Desirably, at least 95% by weight of the particles of the active ingredient have an effective particle size in the range of 0.01 to 10 $\mu$m.

Alternatively, the composition may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The RAR antagonist(s) and RXR agonist(s) are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the RAR antagonist(s) and RXR agonist(s) with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the RAR antagonist(s) and RXR agonist(s), stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:pp. 33 et seq (1976)).

Dosaging

By the invention, a RXR agonist can be administered in vitro, ex vivo or in vivo to cells to enhance the cellular response to a RAR antagonist. One of ordinary skill will appreciate that effective amounts of a RAR antagonist and a RXR agonist can be determined empirically and may be employed in pure form or, where such forms exist, in pharmaceutically acceptable salt, ester or prodrug form. The RAR antagonist(s) and RXR agonist(s) may be administered to a patient in need thereof as pharmaceutical compositions in combination with one or more pharmaceutically acceptable excipients. It will be understood that, when administered to a human patient, the total daily usage of the compounds and compositions of the present invention will be decided by the attending physician within the scope of sound medical judgement. The specific therapeutically effective dose level for any particular patient will depend upon a variety of factors including the type and degree of the cellular response to be achieved; activity of the specific RAR antagonist and RXR agonist employed; the specific composition employed; the age, body weight, general health, sex and diet of the patient; the time of administration, route of administration, and rate of excretion of the RAR antagonist and/or RXR agonist; the duration of the treatment; drugs used in combination or coincidental with the specific RAR antagonist and/or RXR agonist; and like factors well known in the medical arts. For example, it is well within the skill of the art to start doses of RAR antagonists and/or RXR agonists at levels lower than those required to achieve the desired therapeutic effect and to gradually increase the dosages until the desired effect is achieved.

For example, satisfactory results are obtained by oral administration of a RAR antagonist and a RXR agonist at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v. Dosaging of the RAR antagonist may be arranged as described in EP 0 661 259 A1, which is incorporated herein by reference in its entirety.

Dosaging may also be arranged in a patient specific manner to provide a predetermined concentration of a RAR antagonist and/or RXR agonist in the blood, as determined by techniques accepted and routine in the art (HPLC is preferred). Thus patient dosaging may be adjusted to achieve regular on-going blood levels, as measured by HPLC, on the order of from 50 to 1000 ng/ml, preferably 150 to 500 ng/ml.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Materials and Methods

The following materials and methods were generally used in all Examples unless otherwise noted.

Determination of Agonistic/antagonistic Activities of RAR-specific Ligands

HeLa reporter cell lines containing a retinoid-inducible luciferase reporter gene (17 m)5-globin-Luc in the stably transfected reporter constructs GAL-RARα, GAL-RARβ or GAL-RARγ were constructed and used as described previously (Chen, J. Y., et al., *EMBO J.* 14:1187–1197 (1995)). Cells were treated with RAR-specific ligands, and luciferase-induced bioluminescence was monitored in vivo using a single-photon-counting camera (Hamamatsu) by seeding equal amounts of cells in 24-well tissue culture plates and incubating them with increasing concentrations of retinoids alone, or in the presence of T-RA to determine the antagonistic potential of the ligands.

Determination of NB4 Cell Differentiation

NB4 cells were obtained from ATCC and were grown in RPMI-1640 (plus 2 mM L-glutamine) containing 100 units/microliter penicillin and streptomycin and 8% fetal bovine serum (FBS). Cells were treated for four days with retinoid(s) or ethanol vehicle, then washed and resuspended at a density of $5 \times 10^5$ cells/ml. 50 microliter aliquots of this suspension were spread over poly-L-lysine coated slides (Sigma, St. Louis, Mo.). After washing with PBS (137 mM NaCl, 2.7 mM KCl, 4.3 mM $Na_2HPO_4$, 1.4 mM $KH_2PO_4$), the cells were fixed for 10 minutes in 2% formalin (37% formaldehyde in 15% methanol in water) at room temperature.

Nitroblue Tetrazolium Determination

Following fixation, cells were washed three times in PBS and were scored by TPA (12-O-tetradecanoyl-phorbol-13-acetate, 200 ng/ml)-induced nitroblue tetrazolium reduction (Sigma Fast BCIP/NBT) for 30 minutes at 37° C. Samples were examined for cellular and nuclear morphology with an optical microscope (Diavert Leitz); the percentage of differentiated cells was determined by counting at least 300 cells for each treatment.

Anti-PML Immunofluorescence Determination

Following fixation, cells were permeabilized with 0.1% Triton X-100 in PBS (buffer A). After washing in PBS, the cells were blocked in 0.5 mg/ml normal goat IgG (Jackson Laboratories, Bar Harbor, Me.) in PBS for 30 minutes at room temperature, and thereafter incubated overnight at 4° C. with a polyclonal anti-PML antibody (the kind gift of Dr. Anne Dejean), diluted in buffer A containing 0.5 mg/ml normal goat IgG (buffer B) at 4° C. After three washes in buffer A, the cells were incubated with donkey anti-rabbit IgG (H+L) conjugated with cyanine 3 (Jackson Laboratories, Bar Harbor, Me.) in buffer B for 1 hour at room temperature. Following washes in PBS the mounted samples were examined with a confocal laser microscope (TCS, Leica) equipped with cyanine optics for PML localization.

Determination of NB4 Cell Apoptosis

Flow Cytometric Analysis

The cell cycle distribution and presence of "sub-2N" cells and particles in control and retinoid-treated NB4 cells were determined by cell cycle flow cytometry based on DNA content, using an EPICS Profile II cell sorter (Coulter Electronics, Inc., Hialeah, Fla.) equipped with a 15 watt argon laser tuned to an excitation wavelength of 488 nm and filter sets providing an emission wavelength of 575 nm. Cultures of untreated or retinoid-treated cells were centrifuged (250×g) and fixed in 70% ethanol and stored at −20° C. Following two washes in PBS, the cells and subcellular particles were incubated in 1 mg/ml RNase A (59 Kunitz units/mg, Sigma Chemical Co., St. Louis, Mo.) for 30 minutes at 37° C., centrifuged and resuspended in PBS at a concentration of approximately 106 cells per ml. Ethidium bromide was added to a final concentration of 50 micrograms/ml immediately prior to sample analysis.

DNA Fragmentation Analysis

The induction of apoptosis by retinoids was also determined by the appearance of a "ladder" of fragmented DNA as previously described (Nagy, L., et al., *Mol. Cell. Biol.* 15:3540–3551 (1995)). Cells were refed with fresh media and retinoids every 2 days, and the cell density was maintained well below saturation in order to prevent cell death due to nutrient and/or mitogen depletion. Five micrograms per lane of DNA was electrophoresed in a 1.5% agarose gel, followed by staining with ethidium bromide, and DNA bands were visualized and photographed via ultraviolet illumination of ethidium bromide fluorescence.

In vivo RARβ2 Footprinting and RARβ, γ Expression Ligation-mediated PCR

NB4 cells were cultured as described above. P19.6 cells were obtained from ATCC and were cultured in Dulbecco's modified Eagle's medium containing 5% normal FBS and 5% delipidated FBS. NB4 cells were treated with either ethanol or the indicated retinoids (FIG. 6) for 24 hours. After washing in PBS, the cells were treated with 0.1% dimethylsulfate (DMS; Aldrich) for 5 minutes at room temperature. High molecular weight DNA was extracted and cleaved with piperidine. DMS treatment in vitro of naked DNA was done as described (Mueller, P. R., and Wold, B., *Science* 246:780–786 (1989)). Ligation-mediated polymerase chain reaction (LM-PCR) was performed as described (Garrity, P. A., and Wold, B. J., *Proc. Natl. Acad. Sci. USA* 89:1021–1025 (1992)), except that DEEPVENT™ (exo⁻) DNA polymerase (New England BioLabs, Beverly, Mass.) was used. Oligonucleotides used in LM-PCR to detect interactions on the coding strand were:

a.) Human RARβ2 Promoter primer 1: 5'-CCCCCTTTGGCAAAGAATAGAC-3'(SEQ ID NO:1)

primer 2: 5'-AGAATAGACCCTCCTGCCTCTGA
AC-3' (SEQ ID NO:2)

primer 3: 5'-ACCCTCCTGCCTCTGAACAGCTCA
CTTC (SEQ ID NO:3)

b.) Mouse RARβ2 Promoter primer 1: 5'-CCCCCTTTGGCAAAGAATAGAC-3'(SEQ ID NO:1)

primer 2: 5'-AGAATAGACCCTCCTGCCTCGG
AG-3' (SEQ ID NO:4)

primer 3: 5'-ACCCTCCTGCCTCGGAGCAGCT
CACTT-3' (SEQ ID NO:5)

Each primer 3 (SEQ ID NOs: 3 and 5) was labeled at the 5' end with [γ-³²P]ATP using T4 polynucleotide kinase. After PCR, labeled products were resolved in a 4.8% sequencing gel and gels were dried and exposed to X-ray film for production of autoradiograms.

Reverse Transcriptase PCR

Total RNA was isolated and reverse transcribed in a buffer solution comprising 10 mM Tris-HCl (pH 8.3), 50 mM KCl, 2 mM MgCl₂ and 1 mM of all four deoxynucleoside triphosphates, using 25 units of AMV reverse transcriptase in the presence of 50 units of RNAsin for 60 minutes at 42° C. For reverse transcription, 25 picomoles per reaction of the common antisense primer 5'-GACATGCCCACTTCAAAGCACTTC-3' (SEQ ID NO:6) for either RARα, β or γ was used. For each PCR reaction the common antisense primer, one-fourth of the reverse transcribed product and the following specific sense primers were used:

human RARα: 5'-ACCCCCTCTACCCCGCATC
TACAAG-3' (SEQ ID NO:7)

human RARβ: 5'-CTCGTCCCAAGCCCCCCAT
CT-3' (SEQ ID NO:8)

human RARγ: 5'-ACAAGCCATGCTTCGTGTG
CAAT-3' (SEQ ID NO:9)

The amplification was carried out in a final volume of 0.1 ml, using Taq DNA polymerase (Perkin Elmer Cetus) according the manufacturer's instructions. Eighteen PCR cycles (30 seconds at 94° C., 30 seconds at 65° C. and 30 seconds at 72° C.) were performed, and a 10 microliter aliquot of each reaction was analyzed by electrophoresis on a 6% native polyacrylamide gel, which was then stained with ethidium bromide and examined by ultraviolet illumination.

Example 1

RAR- and RXR-induced Activation

Receptor-selective synthetic retinoids (Chen, J.-Y., et al., *EMBO J.* 14:1187–1197 (1995)) (FIG. 1) were used to investigate the contributions of RARα/PML-RARα, RARβ, RARγ and RXRs to the molecular and cellular events which lead to NB4 (Lanotte, M., et al., *Blood* 77:1080–1086 (1991)) cell differentiation upon T-RA treatment. As shown in Table 1, the agonist Am80, which is RARα-specific at ≦1 nM (Chen, J.-Y., et al., *EMBO J.* 14:1187–1197 (1995)), efficiently induced differentiation. Retinoids lacking RARα agonistic activity (Compound A and Compound C; Chen, J.-Y., et al., *EMBO J.* 14:1187–1197 (1995)); Compound B and Compound D, FIG. 1; SR11237 (Lehmann, J. M., et al., *Science* 258:1944–1946 (1992)), were ineffective on their own (Table 1, FIGS. 3b, c). Compound C is the compound described in Example 23 of European Patent Application No. EP 0 661 259, which is incorporated by reference herein in its entirety. Compound D is the compound described in Example 1 of European Patent Application No. EP 0 747 347, which is incorporated by reference herein in its entirety. Moreover, the differentiation induced by 1 nM Am80 was completely blocked by an excess of Compound B, a pure RARα antagonist (not shown). These results demonstrate that inducing the transcriptional activity of AF-2 of either the non-fused RARα allele and/or the RARα moiety of PML-RARα is sufficient to relieve the differentiation block resulting from the formation of a PML-RARα fusion protein. Note that AP1 transrepression by RARα is unlikely to play a critical role in RA-induced NB4 cell differentiation, since "dissociated" retinoids, such as Compound A, albeit efficiently repressing AP1 activity via all three RARs (Chen, J-Y, et al., *EMBO J.* 14:1187–1197 (1995)), did not induce differentiation on their own (FIG. 2b, and not shown).

Figure 4A:
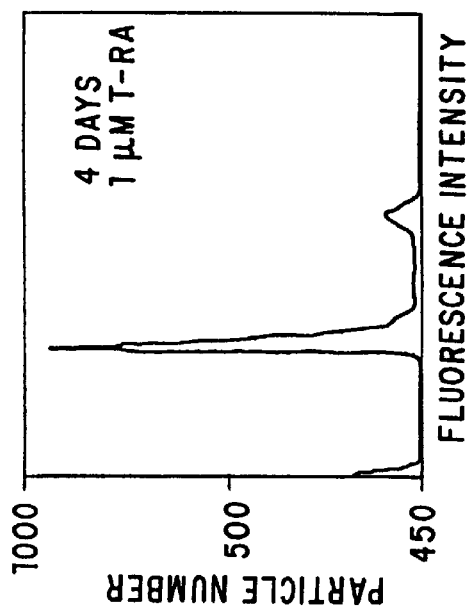
FIGS. 4A–4H. Synergy between RARα agonists or antagonists and RXR agonists for the induction of NB4 cell apoptosis. Effects of retinoids on cell cycle distribution and appearance of "sub-2N" apoptotic cells and particles, as revealed by flow cytometric analysis. The horizontal axis in each histogram indicates the integrated fluorescence intensity and the vertical axis indicates number of particles. Approximately 20,000 particles are represented in each histogram. Histograms indicating the number of cells containing a 2N, 4N or intermediate quantity of DNA for untreated NB4 cells (a), cells treated with 1 mM T-RA for 4, 6 or 8 days (b–d), 1 nM Am80 for 4 or 8 days (e, f), or the combination of 100 nM of Compound A and 100 nM of SR11237 for 4 or 8 days (g, h).
Figure 4B:
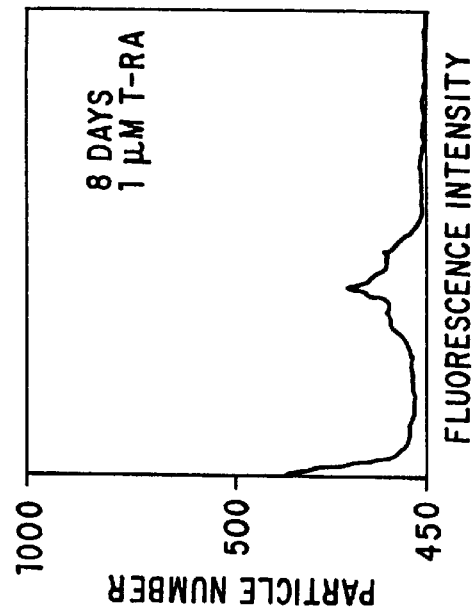
Figure 4C:
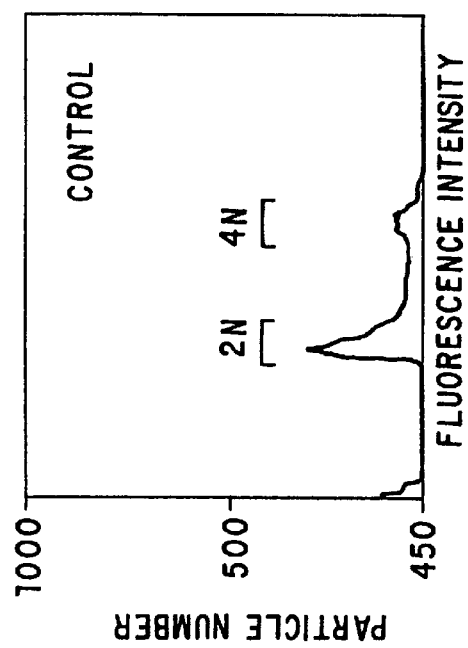
Figure 4D:
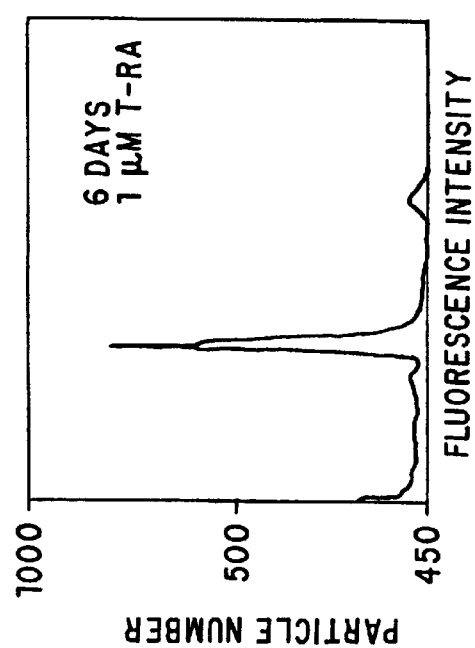
Figure 4E:
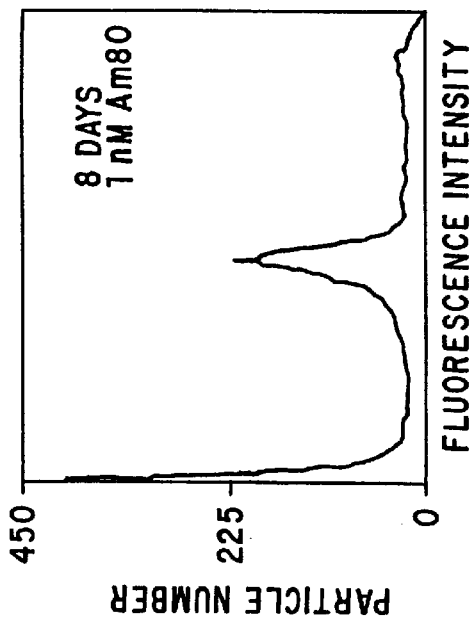
Figure 5:
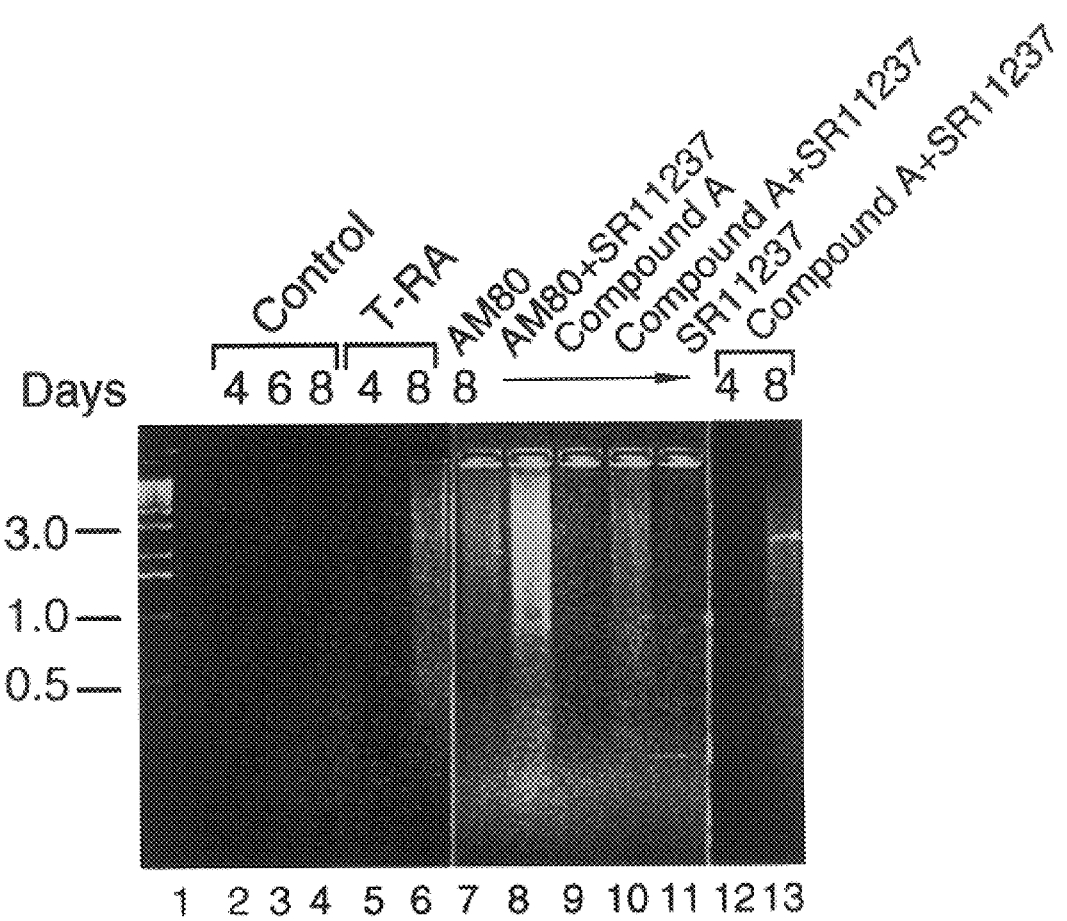
FIG. 5. Retinoid induction of apoptosis in NB4 cells. Photomicrograph of an ethidium bromide-stained agarose gel in a DNA fragmentation assay, performed with cells grown in the absence (lanes 2–4) or presence (lanes 5–13) of the indicated retinoids at the following concentrations: T-RA, 100 nM; Am80, 1 nM; SR11237, 100 nM; Compound A, 10 nM (lanes 9 and 10) and 100 nM (lanes 12 and 13).

After 4 days of treatment with T-RA or RARα agonists, FACS analysis showed that NB4 cells had reduced mitotic activity and accumulated in G1/G0 (FIGS. 4b and e). At day 6, sub-2N particles accumulated in T-RA-treated cultures (FIG. 4c) and at day 8 massive DNA fragmentation indicated extensive apoptosis (FIGS. 4d, f, and FIG. 5, lanes 6, 7). Note that forward and side scatter analysis of the same cell preparations confirmed these results (not shown). As in the case of differentiation, only RARα (but not RARβ or RARγ) agonists could induce this sequence of events (Table 1, and not shown).

Figure 6A:
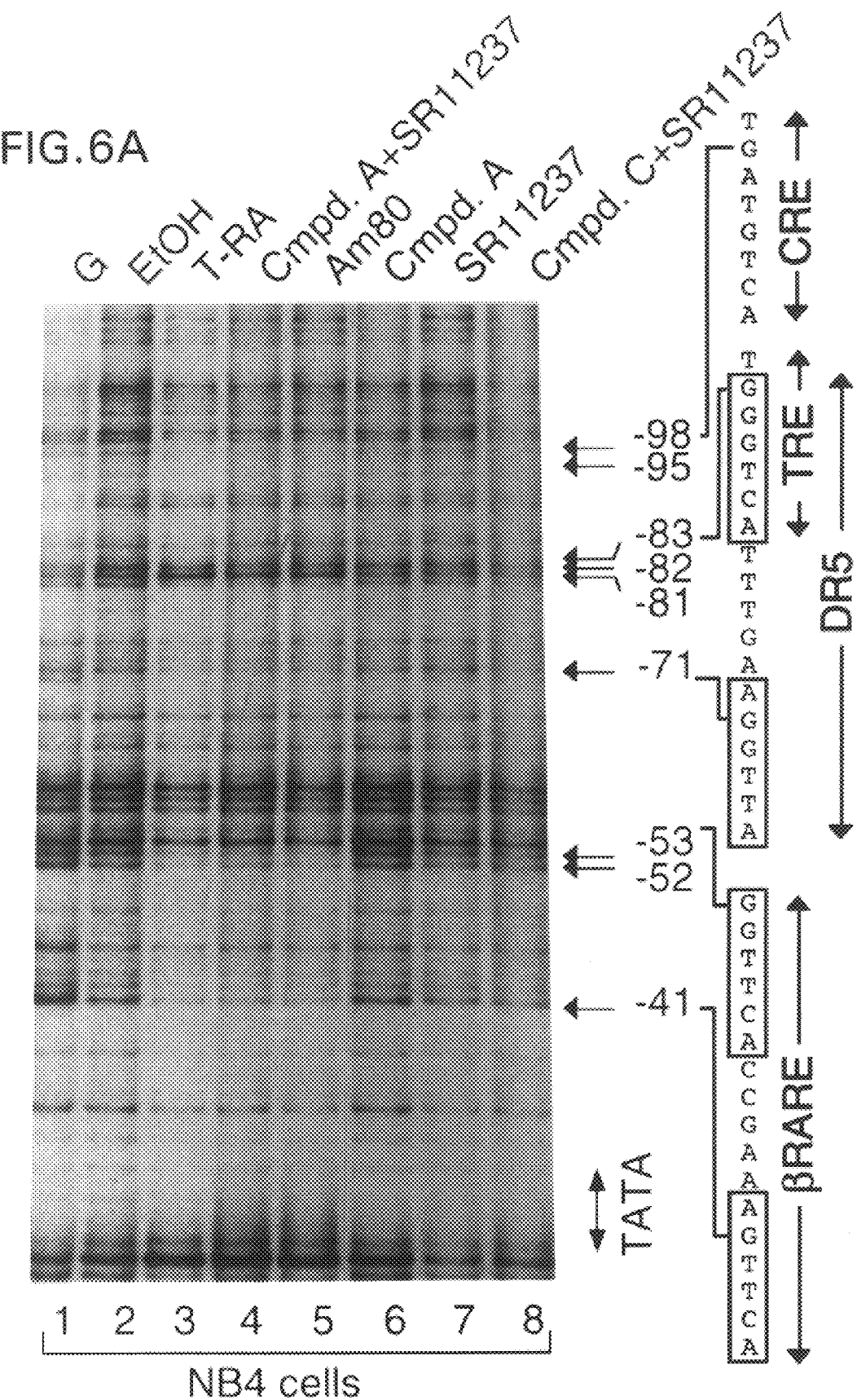
FIGS. 6A–6C. Photographs of sequencing gels demonstrating synergism of RARα and RXR. Cells were treated with agonists as indicated, then processed as described below for ligation-mediated PCR (a, b) or reverse transcriptase PCR (c) and resolved on a sequencing gel. (a) NB4 cells, autoradiogram; (b) P19 cells, autoradiogram; (c) NB4 cells, ethidium bromide-stained gel (RNA transcripts of the β-actin gene were used as control).
Figure 6B:
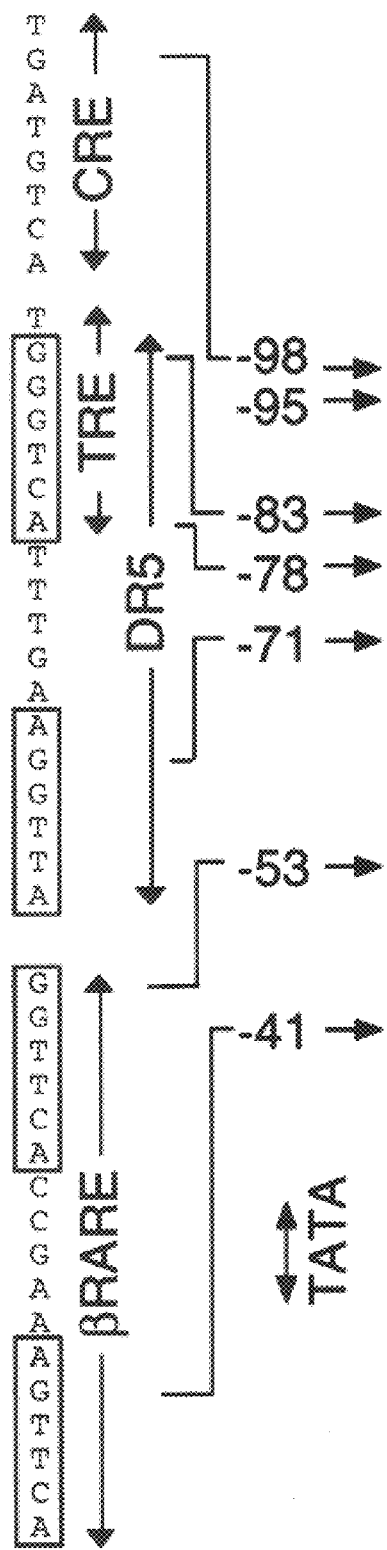
Figure 6B:
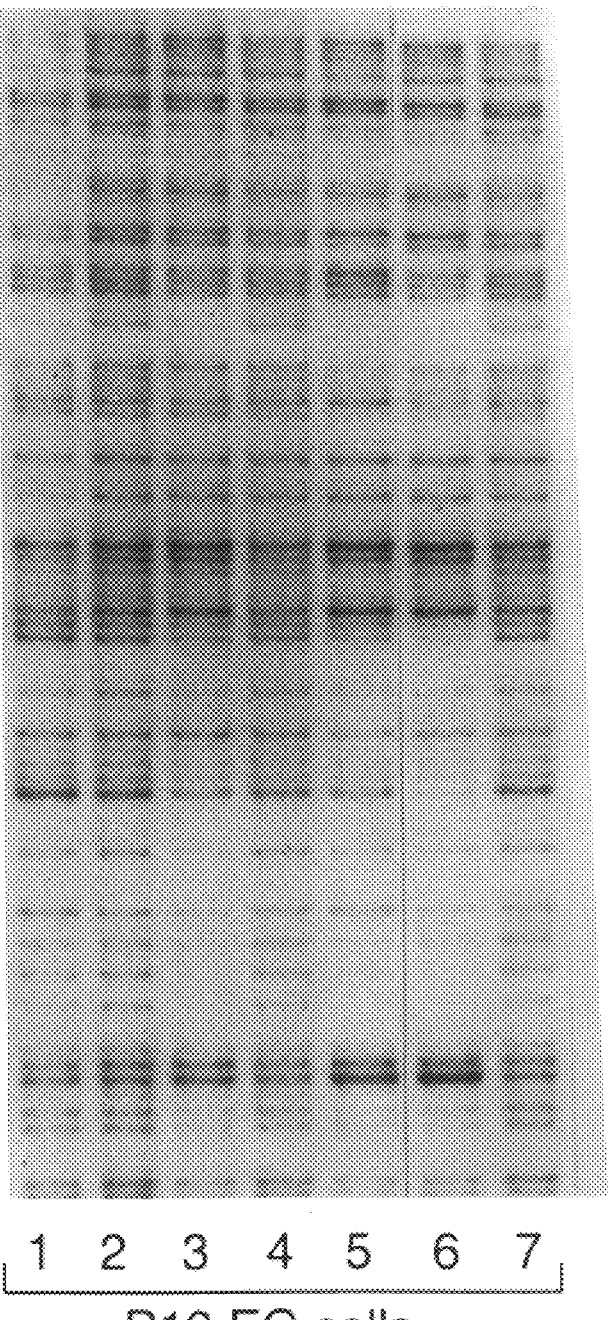
Figure 6C:
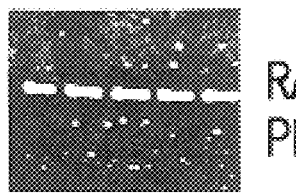
Figure 6C:
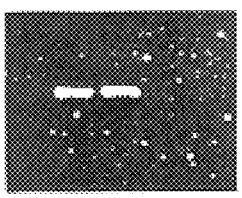
Figure 6C:
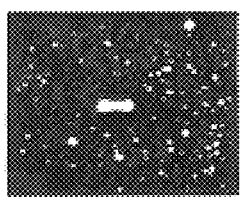
Figure 6C:
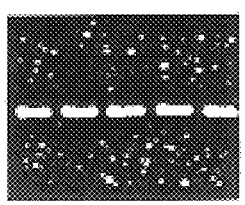

Prior to differentiation, and as previously reported (Dyck, J. A., et al., *Cell* 76:333–343 (1994); Weis, K., et al., *Cell* 76:345–358 (1994); Koken, M. H., et al., *EMBO J.* 13:1073–1083 (1994)) for T-RA, RARα agonists induced the association of endogenous PMUPML-RARα with nuclear bodies (FIG. 3e), while RARα antagonists did not (FIG. 3f, and data not shown). Moreover, in vivo DNA footprinting showed that occupation of the DR5-type retinoic acid response elements (DR5-RAREs) present in the RARβ2 promoter, as well as the recruitment of other promoter-binding factors, was induced by RARα agonists, but not antagonists (FIG. 5, lanes 3, 5 and 6). Apart from minor differences, these footprints were nearly indistinguishable from those originally reported for mouse P19 embryonal carcinoma cells (Dey, A., et al., *Mol. Cell. Biol.* 14:8191–8201 (1994)) (FIG. 6b, lanes 3, 6, 7). The Am80O-induced expression of RARβ2 (and RARγ) was confirmed by RT-PCR (not shown); no induction was seen with RARα antagonists alone (Compound A in FIG. 6c, and not shown).

bodies which was indistinguishable from that seen in presence of RARα agonists (FIGS. 3g and h). Moreover, occupation of the RARβ2 RARE and factor recruitment (Dey, A, et al., *Mol. Cell. Biol.* 14:8191–8201 (1994)) to the RARβ2 promoter in vivo was also induced when cells were treated with Compound A and SR11237 (FIG. 6a). This treatment led to an efficient accumulation of RARβ and RARγ mRNA (FIG. 6c). In keeping with its inability to synergize with

| | | | | | | | | | | +100 nM SR11237 | |
| --- | --- | --- | --- | --- | --- | --- | --- | --- | --- | --- | --- |
| Retinoid | T-RA | 9C-RA | Am80 | Compound A | Compound B | Compound C | Compound D | SR11237 | Am80 | Compound A | Compound B |
| 0.1 | —[1] | — | <1 | — | — | — | — | — | <1 | — | — |
| 0.3 | — | — | <1 | — | — | — | — | — | 20 | — | — |
| 0.5 | — | — | <1 | — | — | — | — | — | 40 | — | — |
| 1 | <1 | <1 | 80 | — | — | — | — | — | 80 | <1 | <1 |
| 10 | <1 | 4 | 81 | — | — | — | — | — | — | 65 | 3 |
| 100 | 81 | 65 | 80 | — | — | — | — | — | — | 78 | 5 |
| 1000 | 80 | 70 | — | <1 | <1 | <1 | <1 | <2 | — | — | 10 |

Percentage of NB4 cells differentiated

[1]"—" = not done.

Example 2

Synergism between RAR- and RXR-specific Ligands

The possible role of RXR in the above events, beyond that of a mere partner for heterodimerization, was investigated by analyzing whether RAR- and RXR-specific ligands could synergize. Indeed, in the presence of the RXR-specific agonist SR11237, Am80 was significantly more efficient at inducing differentiation at low concentrations (Table 1; note that SR11237 alone did not induce differentiation; FIG. 3c). Strikingly and unexpectedly, in combination with SR11237 even the RARα antagonist Compound A induced differentiation with higher efficiency than T-RA or 9C-RA (Table 1; FIG. 3d). It is unlikely that this differentiation could be due to autoinduction of RARβ2 by the RARβ-agonistic activity (FIG. 1) of Compound A in the presence of SR11237, since Compound C (FIG. 1), a stronger RARβ agonist than Compound A (Chen, J-Y, et al., *EMBO J.* 14:1187–1197 (1995)), did not synergize with SR11237 to induce RARβ2-promoter occupancy (FIGS. 6a, b), RARβ2 mRNA production or differentiation (not shown). In addition, Compound B, a "pure" RARα antagonist which does not bind RARβ or RARγ (FIG. 1), also induced differentiation in presence of SR11237, while the RARγ(β) agonist Compound D, which cannot bind RARα, did not (Table 1 and not shown). The lower efficiency of Compound B relative to Compound A may be related to its lower binding affinity for RARα (FIG. 2, and not shown).

Figure 4G:
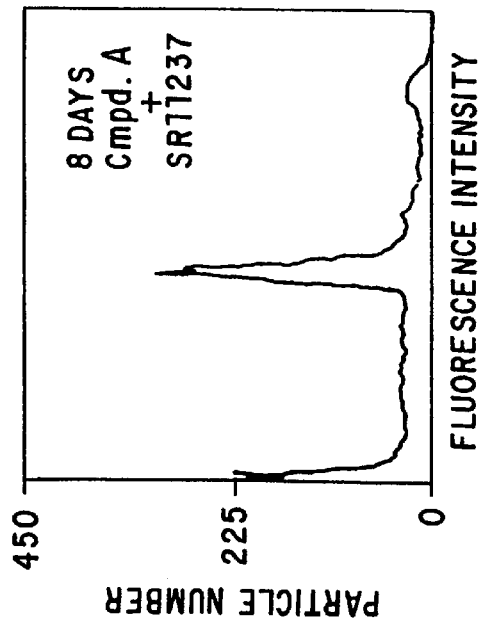
Figure 4F:
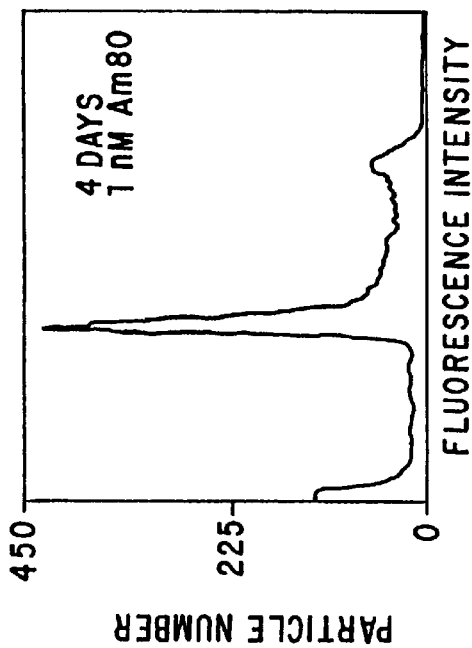
Figure 4H:
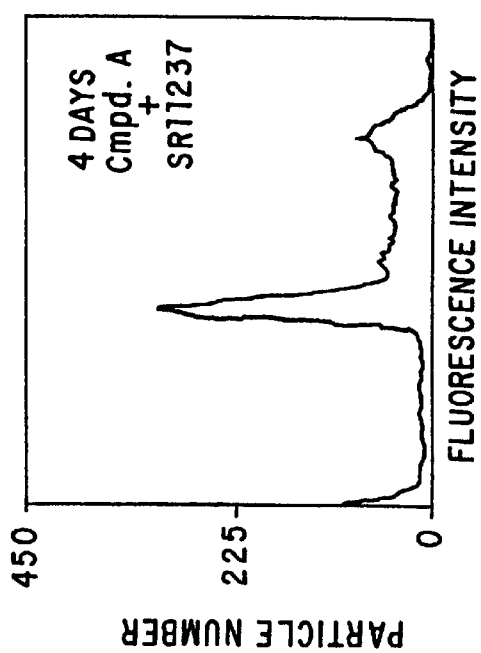

Together the above results clearly indicate that RARα (or PML-RARα) is specifically involved in the synergistic induction of differentiation in presence of the RXR agonist. Synergy between RARα and RXR ligands was not only observed for differentiation, but also for subsequent apoptosis. This was demonstrated by the strong antiproliferative and apoptotic effect of a combination of the RARα antagonist Compound A together with the RXR agonist SR11237, each of which was inefficient alone (FIGS. 4g and h, FIG. 5; and forward and side scatter analysis, not shown). Compound A/SR11237-induced differentiation and apoptosis was preceded by an association of PML-RARα with nuclear SR11237 for differentiation, the other RARα antagonist/RARβ agonist Compound C was neither able to induce nuclear body association of PML-RARα (not shown) nor RARβ2 promoter occupancy (FIG. 6a).

General Discussion

It has previously been suggested that the RXR ligand-dependent transcription activation function AF-2 is silent in RAR-RXR receptor heterodimeric signaling complexes (Kurokawa, R., et al., *Nature* 371:528–531 (1994); Forman, B. M., et al., *Cell* 81:541–550 (1995); Mangelsdorf, D. J., and Evans, R. M., *Cell* 83:835–850 (1995)). In contrast, the present results demonstrate that in cultured NB4 human acute promyelocytic leukemia (APL) cells, in vivo footprints of the RARβ2 promoter RA response element and RARβ2 mRNA expression can be induced not only by treatment with RARα- (and not RARβ-, RARγ- or RXR-) specific retinoids alone, but also by the combination of certain RARα antagonists with a pure RXR agonist. Moreover, such combinations induce the relocation of PML to nuclear bodies and NB4 cell differentiation prior to apoptosis. These results indicate that the effects exerted by retinoids on APL cells are mediated by heterodimers between RARα (or PML-RARα and RXRs), in which the AF-2 of only one partner needs to be transcriptionally competent. Thus, RARα agonists induce two separable events. One event that is required for binding of RXR-RARα heterodimers to DNA in vivo and allows the RXR AF-2 to be activated by agonists can be induced by either a RARα agonist or certain RARα antagonists, whereas the other event which induces RARα AF-2 activity can be exerted by RARα agonists only.

The synergism between RAR and RXR ligands is difficult to reconcile with the conclusion of previous reports (Kurokawa, R., et al., *Nature* 371:528–531 (1994); Forman, B. M., et al., *Cell* 81:541–550 (1995)) that RXR is a transcriptionally silent partner in RXR-RAR heterodimers on both DR1 and DR5 RAREs (reviewed in Mangelsdorf, D. J. and Evans, R. M., *Cell* 83:835–850 (1995)). Specifically, how could a heterodimer comprising an antagonist-bound RARα and an agonist-bound RXR bind to and activate transcription from the RARβ2 promoter, if RXR were unable to bind its ligand when associated with DNA? In fact, one of the above reports (Forman, B. M., et al., *Cell* 81:541–550 (1995)) distinguishes between the inhibitory effects of ligand-free and ligand-bound RAR on RXR activity. Moreover, in contrast to the above reports (Kurokawa, R., et al., *Nature* 371:528–531 (1994); Forman, B. M., et al., *Cell* 81:541–550 (1995)), more recent studies (Kersten, S., et al., *Biochemistry* 35:3816–3824 (1996); Apfel, R., et al., *J. Biol. Chem.* 270:30765–30772 (1995)) have concluded that both partners of RXR-RAR heterodimers bind their cognate ligand irrespective of their binding to DNA, thus supporting the previous conclusion drawn from transfection experiments that both partners can be transcriptionally active (Durand, B., et al., *Cell* 71:73–85 (1992)). Regardless of what may be the basis of the conflicting in vitro results, it is clear that in vivo the RXR partner of RXR-RAR dimers can respond to an agonistic ligand and, therefore, must bind it. In keeping with this conclusion, in vivo synergism between RAR and RXR agonists has been previously reported (Roy, B., et al., *Mol. Cell. Biol.* 15:6481–6487 (1995); Apfel, R., et al., *J. Biol. Chem.* 270:30765–30772 (1995)).

The present studies show that, at high levels, RAR agonists alone are sufficient to induce the genetic programs leading to differentiation and apoptosis of NB4 cells, as well as transcription from the RARβ2 promoter. In contrast, a RXR agonist was inactive unless it is associated with a RAR agonist or certain RAR antagonists. It appears therefore that (i) the apo-RAR structure in the RXR-RAR heterodimer is incompatible with events which are requisite to transactivation in vivo, and (ii) transactivation by RXR-RAR heterodimer comprises two separable RAR-mediated events. One event that is required for binding of RXR/RARα heterodimers to DNA in vivo and allows the RXR AF-2 to be activated by agonists, can be induced by either a RARα agonist or certain RARα antagonists. The other event induces RARα AF-2 activity and can be exerted by RARα agonists only.

Upon extension of the present results to other RA target genes, the conclusion that one of the two functions exerted by RAR ligands in RXR-RAR heterodimers is requisite for RXR ligands to activate target gene transcription in vivo has important implications. RARs will "dominate" over their RXR partners and the presence of RXR agonists would amplify the effect of, but not substitute for, RAR ligands. Note in this respect that the RXR-specific ligand SR11237 on its own was unable to induce the differentiation and expression of RA target genes in F9 and P19 cells (Roy, B., et al., *Mol Cell. Biol* 15:6481–6487 (1995)). The same may be true for RXR heterodimer-mediated signaling pathways involving thyroid hormones and vitamin D3, while for other RXR heterodimers (Mangelsdorf, D. J. and Evans, R. M., *Cell* 83:835–850 (1995)) RXR ligands may act as independent signaling molecules. The design and study of additional RAR and RXR agonists and antagonists by the methods disclosed herein will indicate whether this concept of "dominance" of RAR over RXR can be generalized, and to what extent other synthetic ligands could overcome or modify this "dominance."

Neither RARα specificity nor the synergism between RARα/Compound A and RXR/SR11237 are NB4 cell- or PML-RARα-specific. Human HL-60 myeloblastic leukemia cells lacking the PML-RARα fusion protein responded like NB4 cells to the various ligand combinations with respect to RARβ2 promoter occupancy, RARβ2 mRNA accumulation and differentiation (not shown).

However, it has been reported that, in contrast to NB4 cells, apoptosis of HL-60 cells cannot be achieved with a RAR agonist only, and specifically requires the presence of a RXR agonist (Nagy, L., et al., *Mol. Cell. Biol.* 15:3540–3551 (1995)). RARβ2 promoter occupancy and RARβ2 mRNA accumulation was also observed in P19 embryonal carcinoma (EC) cells treated with a combination of a RARα antagonist and a RXR agonist (Roy, B., et al., *Mol. Cell. Biol.* 15:6481–6487 (1995)) (FIG. 3b). In marked contrast, in F9 EC cells the same ligand combination induced neither RARβ2 expression nor differentiation (data not shown). Thus, taken together with the ability of "dissociated" retinoids (Chen, J.-Y., et al., *EMBO J.* 14:1187–1197 (1995)) to repress AP1 activity, the present results suggest that it may be possible to initiate complex gene programs in a cell-specific manner by the appropriate choice of (or combination of) synthetic retinoids with predefined characteristics. The selectivity and the synergistic potential of RAR and RXR ligands, which allow drastically reduced concentrations of the individual compounds to achieve biological activity, have considerable promise for extending the therapeutic applications of natural and synthetic retinoids and retinoid analogues.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A pharmaceutical composition comprising an antagonist of at least one RAR subtype, an agonist of at least one RXR subtype and a pharmaceutically acceptable carrier or excipient therefor, wherein said composition is capable of inducing the differentiation of a transformed cell.

2. The composition of claim 1, wherein said RAR antagonist is an RARα antagonist.

3. The composition of claim 2, wherein said RARα antagonist is Compound A or Compound B.

4. The composition of claim 1, wherein said RXR agonist is SR11237.

5. The composition of claim 1, wherein said transformed cell is a primary cancer cell.

6. The composition of claim 1, wherein said transformed cell is an established cell line.

7. The composition of claim 6, wherein said established cell line is selected from the group consisting of HL-60 myeloblastic leukemia cells, NB4 promyelocytic leukemia cells, P19 embryonic carcinoma cells, F9 embryonic carcinoma cells and ras-transformed 3T3 cells.

8. The composition of claim 1, wherein said composition does not comprise an RAR agonist.

9. A pharmaceutical composition consisting essentially of an antagonist of at least one RAR subtype, an agonist of at least one RXR subtype and a pharmaceutically acceptable carrier or excipient therefor.

10. The composition of claim 9, wherein said RAR antagonist is an RARα antagonist.

11. The composition of claim 10, wherein said RARα antagonist is Compound A or Compound B.

12. The composition of claim 9, wherein said RXR agonist is SR11237.

13. The composition of claim 9, wherein said composition is capable of inducing the differentiation of a transformed cell.

14. The composition of claim 13, wherein said transformed cell is a primary cancer cell.

15. The composition of claim 13, wherein said transformed cell is an established cell line.

16. The composition of claim 15, wherein said established cell line is selected from the group consisting of HL-60 myeloblastic leukemia cells, NB4 promyelocytic leukemia cells, P19 embryonic carcinoma cells, F9 embryonic carcinoma cells and ras-transformed 3T3 cells.

17. A pharmaceutical composition comprising an antagonist of at least one RAR subtype, an agonist of at least one RXR subtype and a pharmaceutically acceptable carrier or excipient therefor, wherein said composition does not comprise an RAR agonist.

18. The composition of claim 17, wherein said RAR antagonist is an RARα antagonist.

19. The composition of claim 18, wherein said RARα antagonist is Compound A or Compound B.

20. The composition of claim 17, wherein said RXR agonist is SR11237.

21. The composition of claim 17, wherein said composition is capable of inducing the differentiation of a transformed cell.

22. The composition of claim 21, wherein said transformed cell is a primary cancer cell.

23. The composition of claim 21, wherein said transformed cell is an established cell line.

24. The composition of claim 23, wherein said established cell line is selected from the group consisting of HL-60 myeloblastic leukemia cells, NB4 promyelocytic leukemia cells, P19 embryonic carcinoma cells, F9 embryonic carcinoma cells and ras-transformed 3T3 cells.

* * * * *

UNITED STATES PATENT AND TRADEMARK OFFICE
CERTIFICATE OF CORRECTION

PATENT NO. : 6,653,322 B1 Page 1 of 1
DATED : November 25, 2003
INVENTOR(S) : Chambon et al.

It is certified that error appears in the above-identified patent and that said Letters Patent is hereby corrected as shown below:

Title page,
Item [*] Notice, please insert -- Subject to any disclaimer, the term of this patent is extended or adjusted under 35 U.S.C. 154(b) by 32 days. --

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO.     : 6,653,322 B1
DATED          : November 25, 2003
INVENTOR(S)    : Chambon et al.

Page 1 of 1

It is certified that error appears in the above-identified patent and that said Letters Patent is hereby corrected as shown below:

<u>Title page,</u>
Item [62], Related U.S. Application Data, delete "09/919,318" and insert -- 08/919,318 --.

Signed and Sealed this

Twenty-seventh Day of December, 2005

JON W. DUDAS
*Director of the United States Patent and Trademark Office*

UNITED STATES PATENT AND TRADEMARK OFFICE
CERTIFICATE OF CORRECTION

PATENT NO. : 6,653,322 B1 Page 1 of 1
DATED : November 25, 2003
INVENTOR(S) : Chambon et al.

It is certified that error appears in the above-identified patent and that said Letters Patent is hereby corrected as shown below:

<u>Title page,</u>
Item [*] Notice, delete "32 days" and insert -- 136 days --.

Signed and Sealed this

Sixteenth Day of May, 2006

JON W. DUDAS
*Director of the United States Patent and Trademark Office*

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

CCCCCTTTGG CAAAGAATAG AC                                                    22

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

AGAATAGACC CTCCTGCCTC TGAAC                                                 25

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

ACCCTCCTGC CTCTGAACAG CTCACTTC                                              28

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AGAATAGACC CTCCTGCCTC GGAG                                                  24

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

ACCCTCCTGC CTCGGAGCAG CTCACTT                                               27

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single -continued (D) TOPOLOGY: linear (ii) MOLECULE TYPE: cDNA (xi) SEQUENCE DESCRIPTION: SEQ ID NO: 6:

GACATGCCCA CTTCAAAGCA CTTC                                                  24

(2) INFORMATION FOR SEQ ID NO: 7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

ACCCCCTCTA CCCCGCATCT ACAAG                                                 25

(2) INFORMATION FOR SEQ ID NO: 8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 8:

CTCGTCCCAA GCCCCCCATC T                                                     21

(2) INFORMATION FOR SEQ ID NO: 9:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 9:

ACAAGCCATG CTTCGTGTGC AAT                                                   23